(12) United States Patent
Spath

(10) Patent No.: US 9,228,964 B2
(45) Date of Patent: *Jan. 5, 2016

(54) SYSTEM FOR ALIGNING PATTERNS ON A SUBSTRATE

(71) Applicant: Eastman Kodak Company, Rochester, NY (US)

(72) Inventor: Todd Mathew Spath, Hilton, NY (US)

(73) Assignee: EASTMAN KODAK COMPANY, Rochester, NY (US)

(*) Notice: Subject to any disclaimer, the term of this patent is extended or adjusted under 35 U.S.C. 154(b) by 30 days.

This patent is subject to a terminal disclaimer.

(21) Appl. No.: 14/230,114

(22) Filed: Mar. 31, 2014

(65) Prior Publication Data

US 2015/0276640 A1 Oct. 1, 2015

(51) Int. Cl.
*H01L 29/45* (2006.01)
*G01N 27/04* (2006.01)
*G01N 27/22* (2006.01)
*G01B 7/00* (2006.01)
*B25J 13/08* (2006.01)

(52) U.S. Cl.
CPC .............. *G01N 27/045* (2013.01); *B25J 13/087* (2013.01); *G01B 7/003* (2013.01); *G01N 27/228* (2013.01)

(58) Field of Classification Search
CPC . H01L 29/45; H01L 21/67259; B41J 2/17546
See application file for complete search history.

(56) References Cited

U.S. PATENT DOCUMENTS

| 4,534,288 A | 8/1985 | Brovman |
| 5,617,340 A | 4/1997 | Cresswell et al. |
| 7,450,296 B2 | 11/2008 | Jang et al. |

*Primary Examiner* — Mohammad Choudhry
(74) *Attorney, Agent, or Firm* — J. Lanny Tucker

(57) ABSTRACT

A system for aligning a first and second pattern based on alignment structures is disclosed. The system comprises a first substrate including the first alignment structure. The alignment structure has a different magnitude of the electrical characteristic than the substrate. The system also includes an electrical probe and a controller for controlling the relative position of the probe with respect to the substrate to measure the electrical characteristic at a plurality of positions proximate the substrate. The measured electrical characteristics are used to identify the location of the alignment structure by identifying a difference between the measured electrical characteristic at pairs of the plurality of positions. A controller identifies the location of a second alignment structure formed on a second substrate. A registration mechanism aligns the two substrates using the identified locations of the first and second alignment structures.

16 Claims, 17 Drawing Sheets

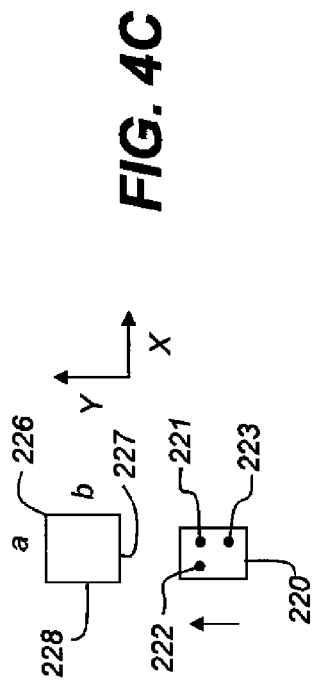
FIG. 4C
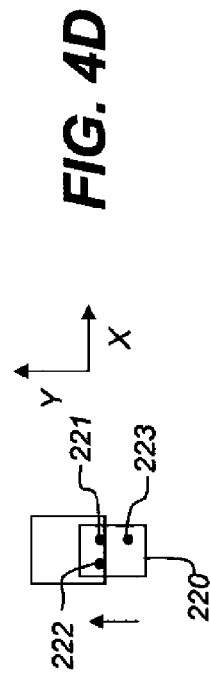
FIG. 4D
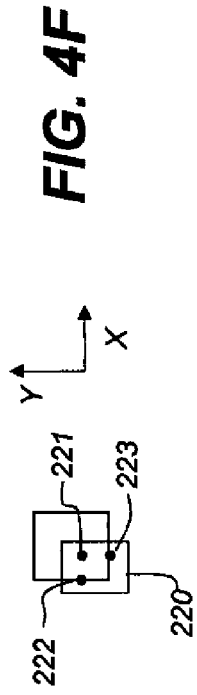
FIG. 4E
FIG. 4F
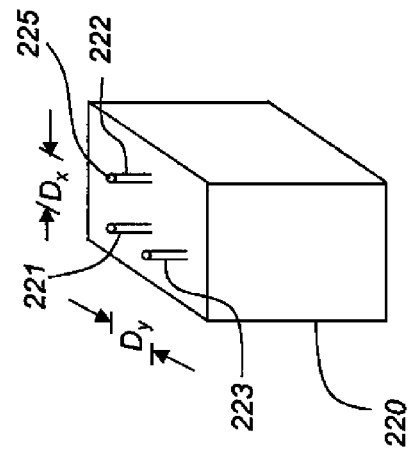
FIG. 4A
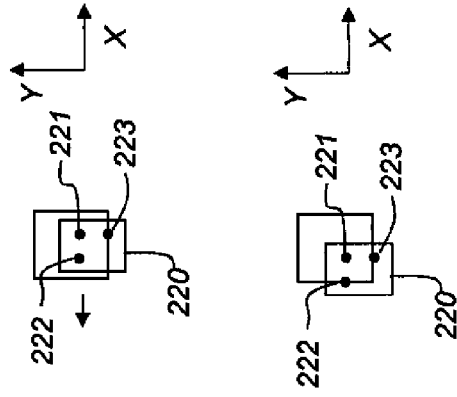
FIG. 4B

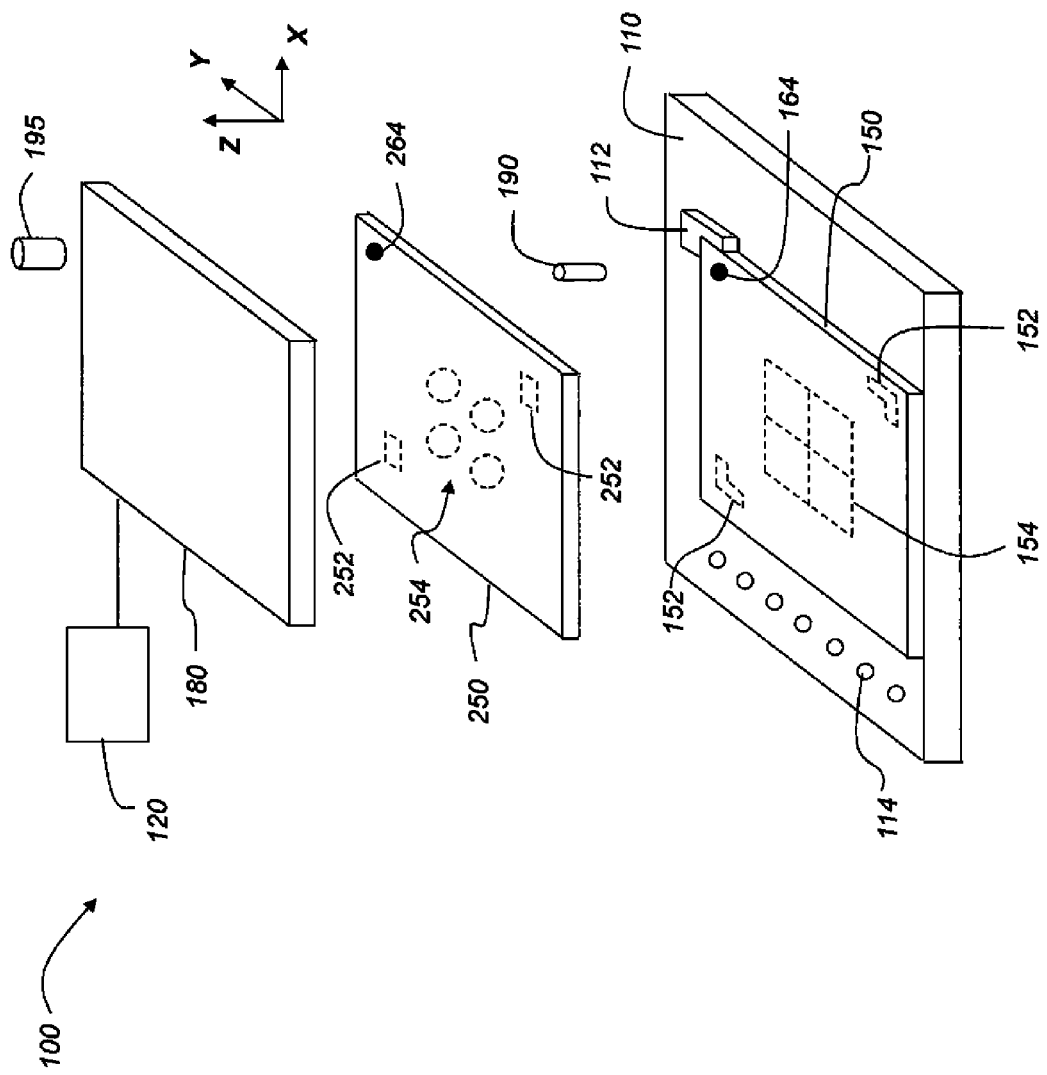

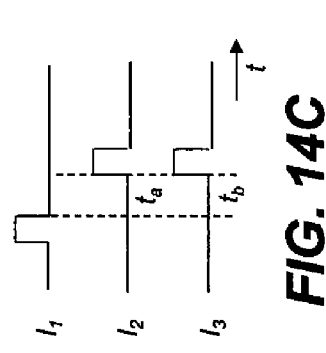
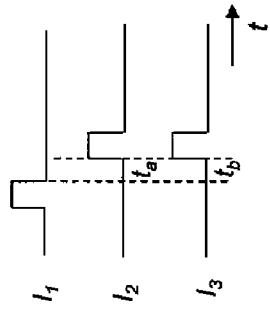
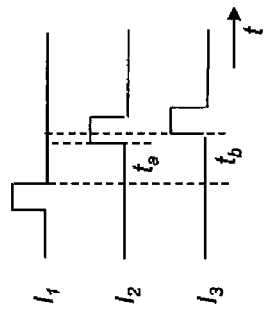
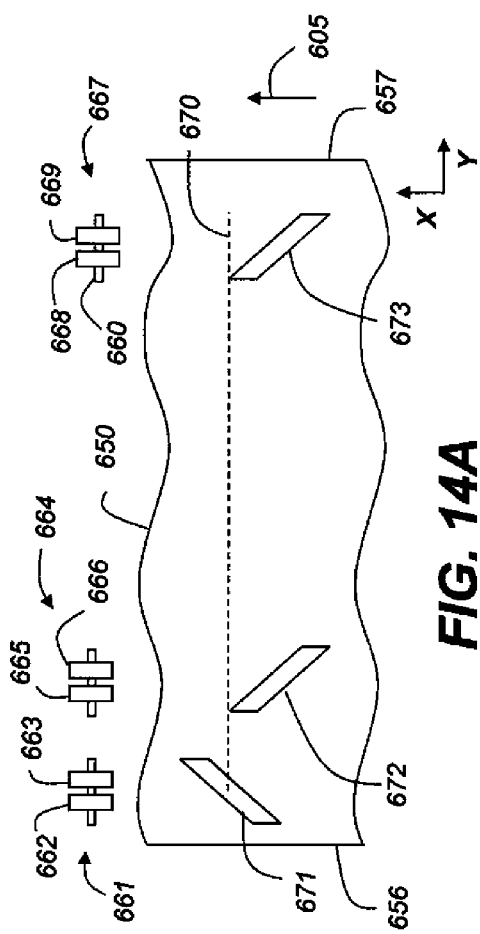
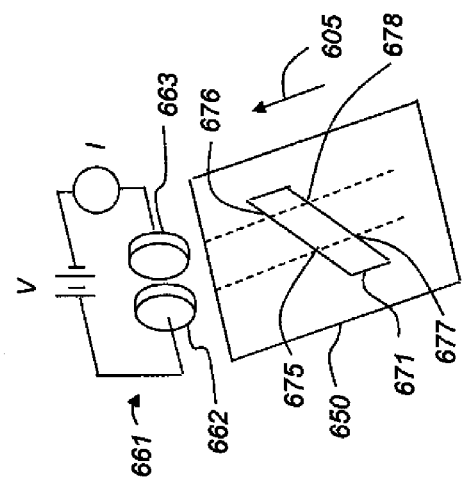

SYSTEM FOR ALIGNING PATTERNS ON A SUBSTRATE

CROSS-REFERENCE TO RELATED APPLICATION(S)

Reference is made to commonly-assigned, U.S. patent application Ser. No. 14/230,107, entitled "METHOD FOR ALIGNING PATTERNS ON A SUBSTRATE", Ser. No. 14/230,127, entitled "METHOD FOR FORMING ALIGNED PATTERNS ON A SUBSTRATE", Ser. No. 14/230,140, entitled "SYSTEM FOR FORMING ALIGNED PATTERNS ON A SUBSTRATE", Ser. No. 14/230,153, entitled "ALIGNMENT STRUCTURE FOR REGISTERING PATTERNS ON A SUBSTRATE", all filed Mar. 31, 2014.

TECHNICAL FIELD

The present invention generally relates to registration of a second pattern with respect to a first pattern, and more particularly to using an alignment structure having a location identified by electrical measurements for the registration.

BACKGROUND

Multi-layer articles, such as multi-layer devices or multi-layer circuits, are typically made as a plurality of layers that are formed in sequence. Multi-layer articles can be made by successive forming of patterned layers on a single substrate, either on one side or on two opposite sides of the substrate. Alternatively, the patterned layers can be formed on a plurality of substrates, and the plurality of substrates can subsequently be assembled together.

Whether a single substrate or a plurality of substrates is used, the patterns in a multi-layer article generally need to be registered with respect to each other. Herein, the terms "registration" and "alignment" refer synonymously to providing a desired geometrical relationship between patterns formed on a substrate. Typically a multi-layer device or circuit has degraded performance if the patterned layers are not registered to within a given set of tolerances.

Conventionally, alignment structures are formed as part of at least one of the patterns of a multi-layer article and the locations of the alignment structures are determined optically. Positioning of a subsequent pattern formed on a substrate, or positioning of a second patterned substrate, is done with reference to the optically determined location of the alignment structures.

Formation of the patterns can be done by additive processing or by subtractive processing. In additive processing the pattern is formed as material is deposited on the substrate. Printing of a pattern is an example of additive processing. Printing can be done in analog fashion, as material is transferred from a master pattern or printing plate to the substrate. Alternatively, printing can be done digitally as a controller controls a printhead, for example, to deposit dots of material at specified locations in order to form the pattern. A familiar example of multi-layer printing is the color printing of images, where successive layers of cyan, magenta, yellow (and optionally black or other color) inks are deposited in registration with each other. In many types of printing systems alignment marks are printed in a first layer near a plurality of edges (typically opposite edges) of the substrate. Cameras or other optical sensing devices are used to monitor the locations of the alignment marks. The analog or digital printing of one or more subsequently printed layers can be controlled using spatial adjustment of the printing device or the substrate so that the subsequent printed layer is registered with reference to the alignment marks. For printing systems where the printhead or the substrate are moved in a nominally linear fashion with respect to each other, the timing of the printing of the subsequent layer(s) can also be controlled on the basis of identified locations of the alignment marks to help provide registration of the patterns. Location of the alignment marks at the outside margins of the substrate can be advantageous both from the standpoints of a) improved angular registration by locating the alignment marks far apart, and b) ability to subsequently remove the margins and the alignment marks in the finished multi-layer article.

Formation of patterns can also be done using subtractive processing. In subtractive processing a blanket layer is typically formed on the substrate. Then material is selectively removed to form the pattern. A familiar example is the processing of semiconductor devices as schematically shown in FIGS. 1A and 1B using a mask aligner 10. A first layer of material can be deposited on the substrate 50. Photoresist 58 can be deposited on the first layer. The photoresist is then exposed with radiation 25 from an exposure station 20 of the mask aligner 10, typically through a first mask 30 having both the desired first pattern 32 and alignment marks 35 and 36 to be associated with the first layer. In the example of FIG. 1A, the pattern 32 is a four by four array of boxes 34 and the alignment marks 35 and 36 are cross-hairs. The photoresist 58 is developed so that the negatives of pattern 32 and the alignment marks 35 and 36 are no longer covered by photoresist. (For simplicity, the positive image rather than the negative image of four by four pattern 52 of boxes 54 and alignment marks 55 and 56 in photoresist layer 58 is shown in FIG. 1A.) The corresponding exposed areas of the first layer of material are subsequently etched away, resulting in the substrate 50 shown in FIG. 1B with the four by four pattern 62 of boxes 64 and cross-hair alignment marks is formed on the surface of the substrate 50. The remaining photoresist 58 is also removed. A second layer (not shown) can then be deposited on the first patterned layer. Photoresist (not shown) can be deposited on the second layer. A second mask 40 is then used to delineate a second pattern 42 in photoresist in registration with the first patterned layer. In particular, cameras 15 of the mask aligner are used to view substrate 50 through second mask 40 as shown in FIG. 1B. The second pattern 42 in this example is a four by four array of circles 44. The desired registration of the second pattern 42 on second mask 40 to the first pattern in this example is when each of the circles 44 is located at the center of a corresponding one of the boxes 64. Mask aligner 10 is used to move second mask 40 or substrate 50 in the X, Y and θ directions until alignment marks 45 and 46 on second mask 40 are registered with corresponding alignment marks 65 and 66 formed in the first layer of material on wafer 50. In the example shown in FIG. 1B, alignment marks 45 and 46 are clear cross-hairs in an opaque field. The clear cross-hairs 45 and 46 are typically designed to be slightly larger than the cross-hairs 65 and 66, so that it is easier to detect when cross-hairs 65 and 66 are centered within clear cross-hairs 45 and 46.

Optical alignment of a sequence of patterned layers works very well when the reference alignment structures can be readily detected optically. For example, if the alignment features have a significantly different reflectance or color than the substrate on which they are formed, then there is effective optical contrast between the alignment features and the substrate.

In some types of multi-layer articles, patterns are formed using materials that do not have effective optical contrast relative to the underlying substrate. For example, it can be difficult to align with reference to an alignment mark that is formed of a substantially transparent material (that is, substantially transparent for the thickness of the patterned layer). Transparent materials can be used in displays, in optical devices, in touch screen sensor films, in photovoltaic devices, and in transparent electromagnetic shielding, for example.

SUMMARY OF THE INVENTION

What is needed is a way to identify a location of an alignment mark having poor optical contrast with respect to the substrate, and then to use the identified location as a basis for aligning one or more additional patterns with reference to a first pattern.

According to an aspect of the invention, a system for aligning a second pattern to a first pattern based on a first alignment structure having a location identified by measurements of an electrical characteristic comprises a first substrate having the first pattern including the first alignment structure, wherein the first alignment structure has a different magnitude of the electrical characteristic than the first substrate, an electrical probe, a controller for controlling the relative position of the electrical probe with respect to the first substrate to measure the electrical characteristic corresponding to each of a plurality of positions proximate the first substrate, for comparing the measured electrical characteristic as a function of position of the probe to identify the location of the first alignment structure by identifying a difference between the measured electrical characteristic at a pair of the plurality of positions exceeding a predetermined threshold, a second substrate having the second pattern including a second alignment structure formed thereon, a controller for identifying the location of the second alignment structure, and a registration mechanism for aligning the second substrate to the first substrate using the identified locations of the first and second alignment structures.

The invention provides significant advantages over prior art methods and systems. Location of an alignment mark having poor optical contrast with respect to the substrate can be identified, and then used as a basis for aligning one or more additional patterns with reference to a first pattern. The substrates and deposited patterns can be made of transparent or substantially transparent materials enabling applications such as touch-screens.

BRIEF DESCRIPTION OF THE DRAWINGS

Aspects of the invention are better understood with reference to the following drawings. The elements of the drawings are not necessarily to scale relative to each other.

FIG. 4A shows a configuration of a resistance probe unit;

FIG. 4B shows a schematic for measuring resistance via current measurement using the probe unit of FIG. 4A;

FIGS. 4C through 4F show a sequence of moves of the probe unit of FIG. 4A for identifying the location of an alignment structure;

FIG. 5 shows a partially exploded view of a portion of the system of FIG. 2 for aligning a second substrate to a first substrate;

FIG. 14A shows a top view of an alignment structure configuration according to an aspect of the invention;

FIG. 14B shows a schematic for measuring resistance via current measurement; and FIG. 14C shows current readings for the alignment structure configuration of FIG. 14A corresponding to preferred alignment in the cross-track direction with no skew;

FIG. 14D shows current readings corresponding to misalignment in the cross-track direction;

FIG. 14E shows current readings corresponding to skew error;

DETAILED DESCRIPTION

Figures 1A, 1B:
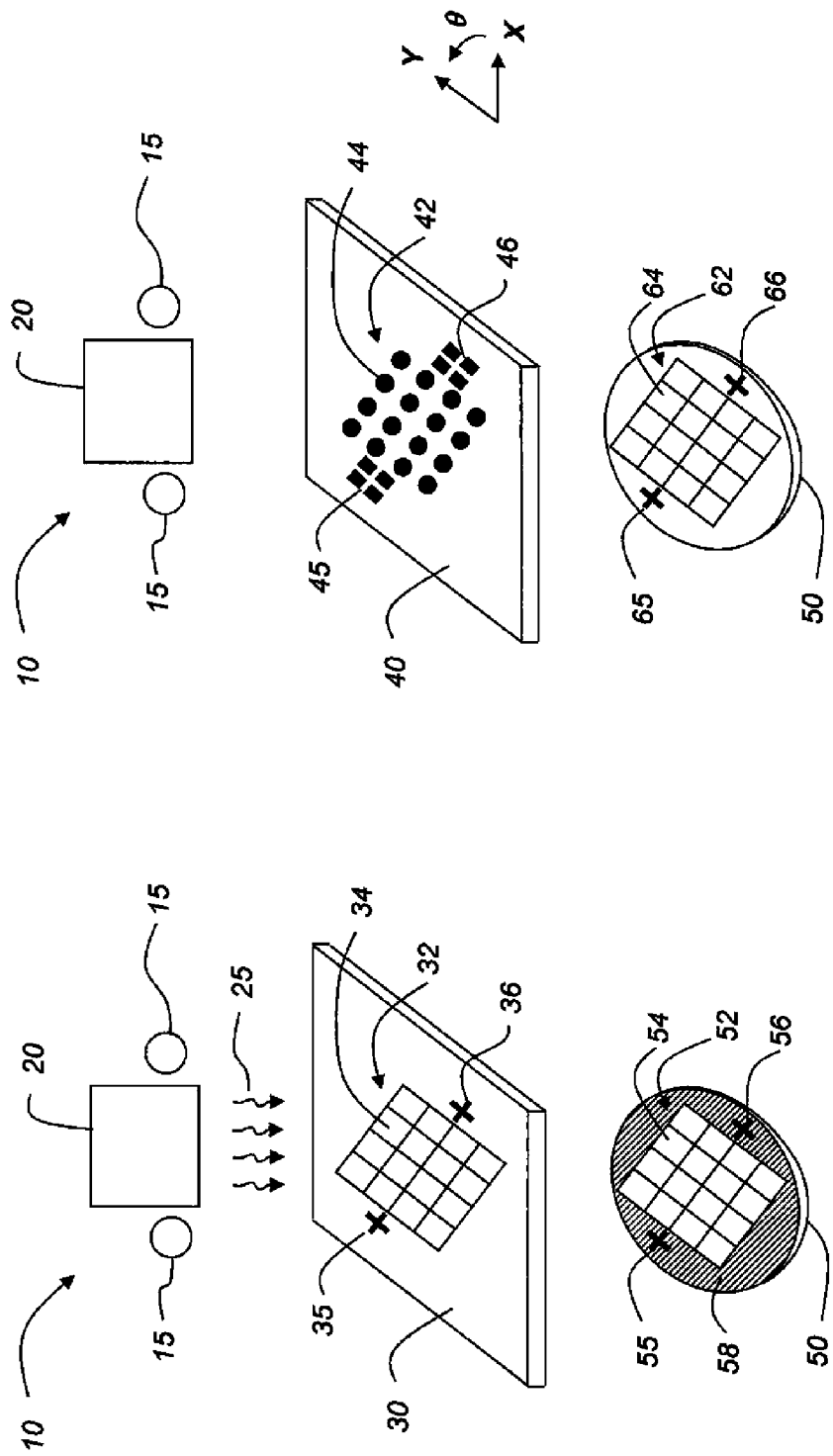
FIG. 1A shows a schematic of a prior art method of exposing a photoresist pattern on a substrate through a first mask for subtractive processing.
FIG. 1B shows a schematic of a prior art method of a aligning a second mask relative to alignment marks formed on the substrate using the first mask of FIG. 1B.

Throughout the specification and claims, the following terms take the meanings explicitly associated herein, unless the context clearly dictates otherwise. The meaning of "a," "an," and "the" includes plural reference, the meaning of "in" includes "in" and "on." Additionally, directional terms such as "on", "over", "top", "bottom", "left", "right" are used with reference to the orientation of the Figure(s) being described. Because components of aspects of the present invention can be positioned in a number of different orientations, the directional terminology is used for purposes of illustration only and is in no way limiting.

The present description will be directed in particular to elements forming part of, or cooperating more directly with, a system in accordance with the present invention. It is to be understood that elements not specifically shown, labeled, or described can take various forms well known to those skilled in the art. In the following description and drawings, identical reference numerals have been used, where possible, to designate identical elements. It is to be understood that elements and components can be referred to in singular or plural form, as appropriate, without limiting the scope of the invention.

The example aspects of the present invention are illustrated schematically and not to scale for the sake of clarity. One of ordinary skill in the art will be able to readily determine the specific size and interconnections of the elements of the example aspects of the present invention.

Aspects of the invention rely on the use of electrical measurements to identify the location of alignment features formed in association with a first pattern for use in aligning one or more additional patterns with reference to the first pattern. This requires that there be effective "electrical contrast" between the alignment structure and the substrate on which it is formed. Electrical properties of materials include resistivity (or conductivity) as well as dielectric constant for example.

Although in general the invention is useful for any combination of substrate material and pattern layer material having poor optical contrast but effective differentiation using appropriate electrical measurements, a particular class of patterned materials of interest is the class of transparent conductive films. Transparent conductive films can be used in displays, in optical devices, in touch screen sensor films, in photovoltaic devices, and in transparent electromagnetic shielding, for example.

Table 1 lists electrical resistivity ρ for a variety of substrate materials. Thermal silicon oxide is a thermally grown oxide layer that is typically formed on silicon to provide electrical insulation. Herein when we refer to forming a pattern on substrate, the substrate can include not only the underlying bulk substrate, but also one or more layers that have previously been formed on the bulk substrate and located below the patterned layer. Table 2 lists electrical resistivity ρ for a variety of transparent conductive films.

TABLE 1

Electrical resistivity ρ for some substrate materials

| Substrate Material | Resistivity (ohm - meter) |
|---|---|
| Silicon | $6.4 \times 10^2$ |
| Thermal silicon oxide | $10^{14}$ |
| Glass | $10^{10}$ to $10^{14}$ |
| Polyethylene terephthalate (PET) | $10^{21}$ |

TABLE 2

Electrical resistivity ρ for some transparent conductive films

| Transparent Conductive Material | Resistivity (ohm - meter) |
|---|---|
| Graphene | $10^{-8}$ |
| PEDOT - PSS | $10^{-3}$ to $10^{-1}$ |
| Indium tin oxide | $10^{-6}$ |

One class of transparent conductive materials is doped metal oxides, such as indium tin oxide (tin-doped indium oxide), aluminum-doped zinc oxide, and indium-doped cadmium oxide. Another class of transparent conductive materials is transparent conducting organic materials including graphene, carbon nanotubes and polymers such as the PEDOT family of materials. PEDOT is the commonly used name for poly(3,4-ethylenedioxythiophene). Doping PEDOT with poly(styrene sulfonate) can improve the properties over the unmodified PEDOT. This PEDOT-PSS compound has become an industry leader in transparent conductive polymers. Where transparency is a desired factor, transparent conductive films can have a light transmittance between 80% and 100%. Transparent conductive polymers can be further advantaged in combination with flexible substrates such as PET, since the transparent conductive polymers can also be flexible.

Figure 2:
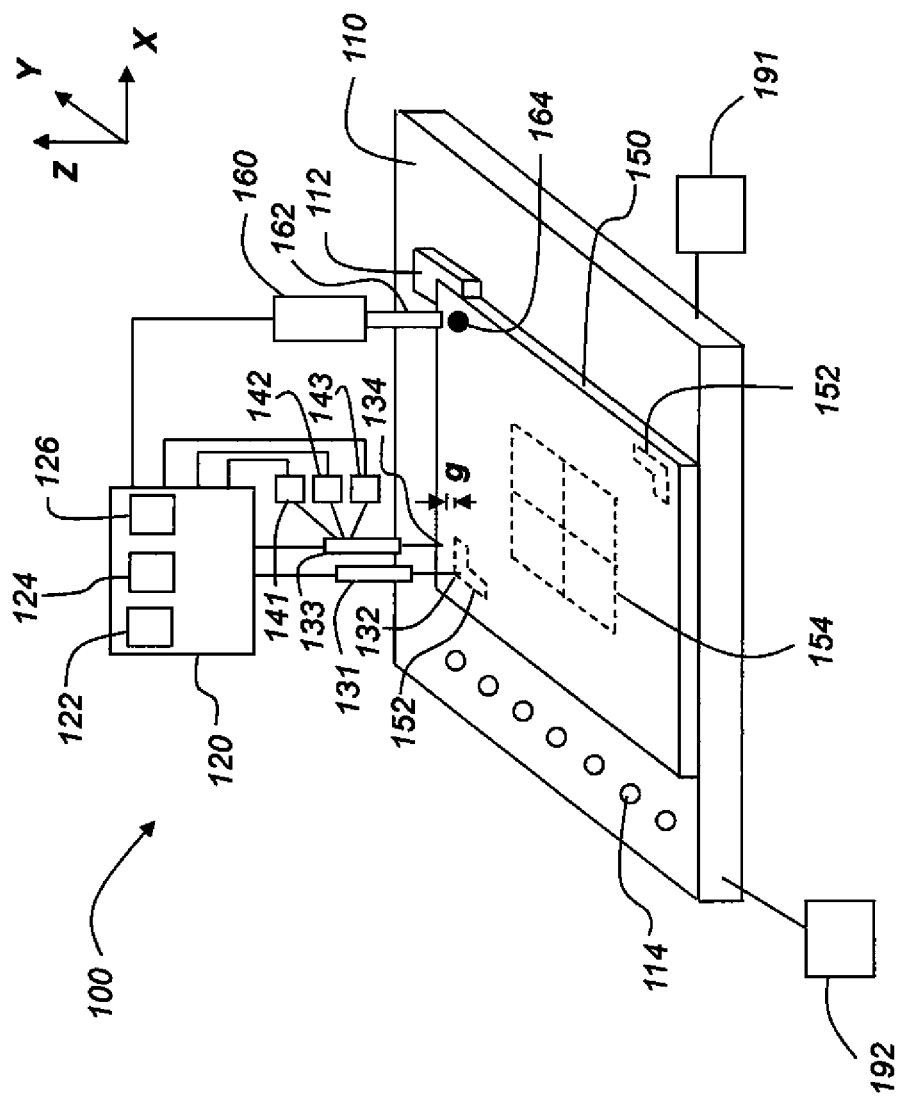
FIG. 2 shows a portion of system 100 for locating a pattern relative to an alignment structure by using measurements of an electrical characteristic according to an aspect of the invention.

FIG. 2 shows a portion of system 100 for locating an alignment structure by measurements of an electrical characteristic for alignment of a pattern. System 100 includes a support 110 disposed along an X-Y plane for a first substrate 150 on which one or more first alignment structures 152 are formed, as well as a first pattern 154. In this example, first alignment structures 152 and first pattern 154 are shown in dashed lines to indicate that they are substantially transparent. Herein substantially transparent is defined as having a light transmittance of 75% or more. Optionally, support 110 includes a mechanical registration feature 112 for coarse alignment of first substrate 150. Also optionally, support 110 includes a hold-down mechanism, such as a vacuum hold-down for holding first substrate 150 in a stationary position. Vacuum holes 114 are shown in FIG. 2 as located beyond the left edge of first substrate 150. Similar vacuum holes (not shown) can be arrayed across the area of support 110 that is covered by first substrate 150. Alternative types of hold-down mechanisms include electrostatic hold-down and mechanical clamps.

System 100 is configured to measure electrical resistance using first probe 131 and second 133. In the aspect of the invention shown in FIG. 2, the first probe 131 is a fixed resistance probe and the second probe 133 is a movable resistance probe. Movable probe 133 is moved to a plurality of positions proximate first substrate 150 for taking the measurements. In the example shown in FIG. 2, system 100 includes a first mover 141 for moving movable probe 133 along the X direction parallel to the support 110, a second mover 142 for moving movable probe 133 along the Y direction parallel to the support 110, and a third mover 143 for moving movable probe 133 along the Z direction perpendicular to the support 110. Controller 120 controls the first, second and third movers 141, 142 and 143 using mover control module 126. In some aspects of the invention, first pattern 154 and first alignment structures 152 have been formed on first substrate 150 with reference to the same or a similar feature as mechanical registration feature 112, so that the approximate position of at least one first alignment structure 152 is known. The first alignment structure 152 has a large enough region that the probe tip 132 of fixed probe 131 can be placed with reasonable confidence on alignment structure 152.

Movable probe 133 is moved to a plurality of positions for taking resistance measurements. Because of the large differences in resistivity between typical substrate materials (Table 1) and typical transparent conductive materials (Table 2) it is easy to distinguish when probe tip 134 of movable probe 133 is in contact with or out of contact with the first alignment structure 152 in contact with fixed probe 131. The resistance measured by the two probes is equal to ρl/wt, where l is the length of the current path (that is, the distance between probe tips 132 and 134), w is the "effective width" of the current path, and t is the thickness of the current path. The effective width of the current path would be the actual width of the alignment structure if the probes were parallel line contacts across a finite width conductive stripe, or if the point contacts were very far apart on a narrow conductor. Using the formula ρl/wt and the actual width will result in some amount of error in a resistance measurement using two probe points. However, for many cases of interest it is not the exact value of the resistance measurement that is of interest, but rather the large change in resistance value when both probes contact the conductive alignment structure relative to one or both probes not contacting the alignment structure. In addition, as described below, in some aspects of the invention, resistance itself is not separately determined. Rather, a current that depends on resistance is measured due to an applied voltage, or a voltage that depends on resistance is measured due to current applied through a current source.

For a layer of substantially constant thickness t (such as the layer forming the first alignment structure), one can refer to the sheet resistance equal to p/t as the electrical characteristic. The thickness of first substrate 150 is typically much thicker (on the order of 0.1 mm to 2 mm) than the thickness (0.001 mm or less) of first alignment structure 152, but the differences in resistivities are sufficient to make it clear when probe tip 134 is in contact with or out of contact with first alignment structure 152. What is actually measured between the two resistance probes is resistance (voltage divided by current). Typically the resistance measured when both probe tips 132 and 134 are contacting first alignment structure 152 is less than 1% of the resistance measured when probe tip 134 is not contacting first alignment structure 152. The location of the first alignment structure 152 can be identified by a change of measured value between measurement locations that exceeds a predetermined threshold. The predetermined threshold can be set to provide effective differentiation by the controllers between the measured electrical characteristic at locations corresponding to the substrate and the alignment structure. In the above example, a threshold corresponding to a change in the resistance of 100 times or more can be used. Although in many cases of interest the alignment structure is more conductive than the underlying substrate, the location of an electrically insulating or resistive alignment structure covering a conductive substrate or surrounded laterally by an electrically conductive layer can also be identified.

An edge of alignment structure 152 can be identified as lying between the position of a measurement of high resistance (probe tip 134 on the surface of first substrate 150) and a measurement of comparatively low resistance (probe tip 134 contacting first alignment structure 152. The closer the two measurement positions are, the more accurately the location of the edge of the alignment structure can be determined. In the example shown in FIG. 2, by moving movable probe 133 along the X direction using first mover 141 and measuring resistance values corresponding to each of a plurality of positions along the X direction, one or more edges of the leg of first alignment structure 152 that extends along the Y direction can be located. Because there can be some manufacturing variation in the width of first alignment structure 152, it can be useful to identify and locate two opposite edges of the leg extending along the Y direction (a first edge on a first side of the leg and a second edge on a second side of the leg) and define the location of the leg of the first alignment structure 152 with respect to a center position midway between the opposite edges of the leg. Similarly, by moving movable probe 133 along the Y direction using second mover 142 and measuring resistance values corresponding to each of a plurality of positions along the Y direction, one or more edges of the leg of first alignment structure 152 that extends along the X direction can be located. Again, because of manufacturing variation in the width of alignment structure 152, it can be useful to identify and locate two opposite edges of the leg extending along the X direction.

In the aspect of the invention shown in FIG. 2, movable probe 133 is raised up during its moves between measurement positions, so that there is a gap g between the probe tip 134 and the surface of first substrate 150. In other aspects of the invention, movable probe tip 134 is held in contact with first substrate 150 during movement between measurement positions.

In addition to mover control module 126 described above, controller 120 also includes measurement module 122 for performing the resistance measurements, and interpreting the resistance measurements for locating first alignment structures 152. Mover control module 126 controls the distance moved by first mover 141 and second mover 142 so that measurement module can analyze resistance as a function of position of movable probe 133. Registration module 124 controls the recording of the location of the first alignment structure for use in aligning one or more additional patterns to first pattern 154. In some aspects of the invention, registration module 124 can include a memory. In other aspects of the invention, registration module 124 controls a marking station 160 for providing at least one reference mark 164 on the first substrate 150 at a predetermined distance and direction from the identified location of first alignment structure 152. Reference mark 164 can be observed optically or it can be used as a mechanical registration mark. Marking station 160 includes a marking element 162 that can include at least one of an ink marker, a laser, a blade, a hole punch, an indenter, a drill or a heated tip.

In some aspects of the invention, rather than moving the probe 133 while keeping the first substrate 150 stationary, the probe 133 is held in a fixed position and the first substrate 150 is moved. FIG. 2 shows an optional first mover 191 for moving the substrate 150 (by moving support 110) in the X direction, and an optional second mover 192 for moving the substrate 150 (by moving support 110) in the Y direction.

Figure 3B:
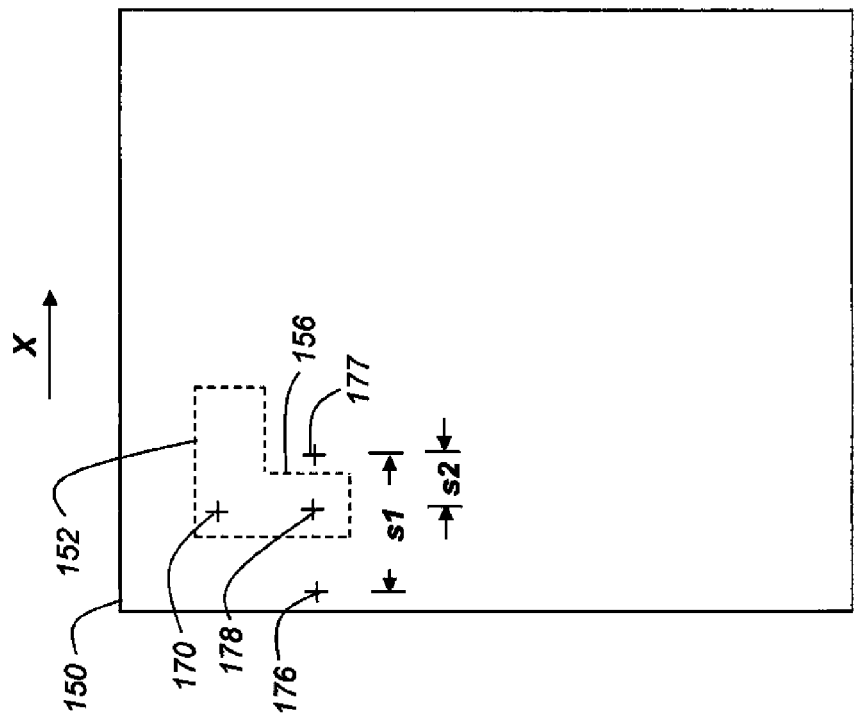
FIGS. 3A and 3B shows sequences of moves of a probe for finding the location of an edge of an alignment structure.
Figure 3A:
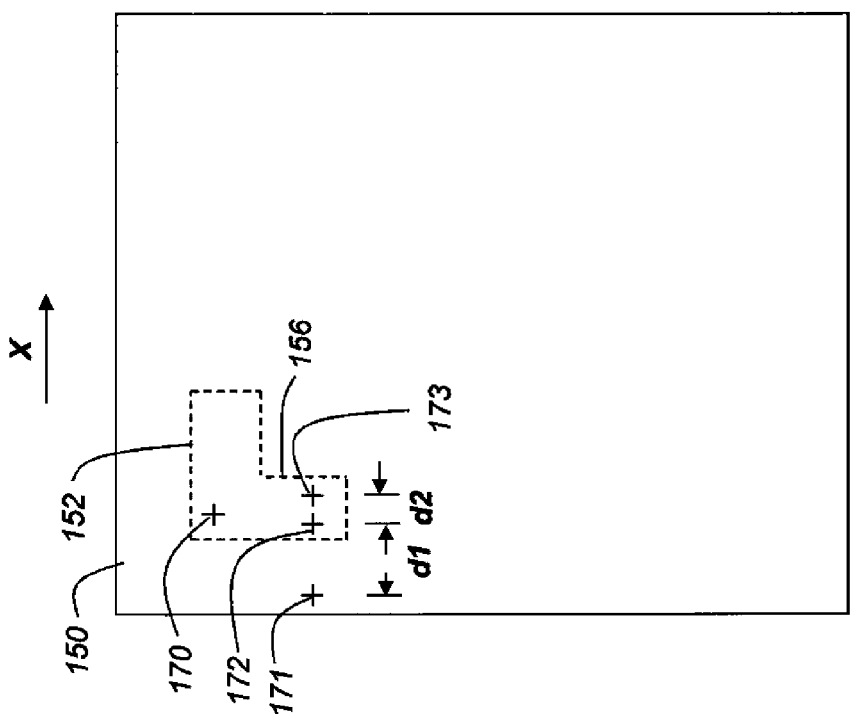

FIG. 3A shows a sequence of moves of movable probe 133 as controlled by controller 120 (FIG. 2) in order to find the location of edge 156 of first alignment structure 152 on first substrate 150, where the distance moved is a function of whether a high value or low value of resistance is measured. In FIG. 3A it is assumed that fixed probe 131 is at contact position 170. Movable probe 133 (FIG. 2) is controlled by controller 120 to take a first measurement of resistance at first position 171. Since, in this example, first position 171 is not in contact with first alignment structure 152, the first measured resistance is a high value. Then movable probe 133 is moved along the X direction by a first distance d1 to second position 172 and a second measurement of resistance is taken at second position 172. Since, in this example, second position 172 is in contact with first alignment structure 152, the second measurement of resistance is a low value. Controller 120 is programmed to know the width of the leg of first alignment structure 152 in the X direction, so as it controls movable probe 133 to move a second distance d2 to a third position 173, the distance d2 moved along X controlled to be less than the known width of the leg. In addition, d2 is typically less than d1 if controller 120 recognizes that movable probe 133 is in already in contact with first alignment structure 152 at second position 172. Movement by a third distance (not shown) along the X direction to a fourth position would typically be less than or equal to second distance d2 if the controller recognizes that movable probe is still in contact with first alignment structure 152 at third position 173. Successive moves and measurements can be made until a high value of resistance is again measured, corresponding to a position (not shown) that is beyond edge 156 of first alignment structure 152.

FIG. 3B shows a sequence of moves of movable probe 133 as controlled by controller 120 (FIG. 2) in order to find the location of edge 156 of first alignment structure 152 on first substrate 150, where a high value of resistance is recorded at both the first and second positions. In FIG. 3B it is assumed that fixed probe 131 at contact position 170. Movable probe 133 (FIG. 2) is controlled by controller 120 to take a first measurement of resistance at first position 176. Since, in this example, first position 176 is not in contact with first alignment structure 152, the first measured resistance in this example is a high value. Then movable probe 133 is moved along the X direction by a first distance s1 (where s1 is larger than the known width of the leg of the first alignment structure 152) to second position 177 and a second measurement of resistance is taken at second position 177. Since, in this example, second position 177 is also not in contact with first alignment structure 152, the second measurement of resistance in this example is also a high value. In the sequence of moves shown in FIG. 3B, the controller 120 (FIG. 2) controls the movable probe to move it by a second distance s2 less than first distance s1 in a direction opposite the X direction. In this example, moving from first position 176 to 177 skips past edge 156 of first alignment structure 152. Moving a smaller distance s2 in the opposite direction results in movable probe 133 contacting first alignment structure 152 at third position 178 so that a low value of resistance is recorded. A succession of moves along the same direction (as in FIG. 3A) or in opposite directions (as in FIG. 3B) can be used iteratively to locate edge 156 with sufficient accuracy.

In some aspects of the invention, the electrical probes can be integrated together in a probe unit. FIG. 4A shows an example of a probe unit 220 having a first contact element 221, a second contact element 222 and a third contact element 223 that are electrically insulated from each other and arrayed in a nonlinear fashion. Each of the contact elements includes a contact surface 225. First contact element 221 can be a reference probe, where second contact element 222 is displaced from first contact element 221 by a distance $D_x$ along the X direction, and third contact element 223 is displaced from first contact element 221 by a distance $D_y$ along the Y direction. FIG. 4B shows an example of a circuit for measuring resistance. What is actually measured is a current whose value depends on the resistance between two contact elements. A first voltage $V_1$ and a first current measuring device $I_1$ are connected between first contact element 221 and second contact element 222. A second voltage $V_2$ and a second current measuring device $I_2$ are connected between first contact element 221 and third contact element 223. If both first contact element 221 and second contact element 222 are in contact with the same conductive surface, such as a conductive alignment structure, then first current measuring device $I_1$ will measure a significantly higher current than if either first contact element 221 or second contact element 222 is not in contact with the same conductive surface. Similarly, if both first contact element 221 and third contact element 223 are in contact with the same conductive surface, such as a conductive alignment structure, then first current measuring device $I_2$ will measure a significantly higher current than if either first contact element 221 or third contact element 223 is not in contact with the same conductive surface.

FIGS. 4C through 4F show a sequence of relative movements of probe unit 220 and an alignment structure 226. With reference to FIG. 2, alignment structure 226 is formed on a substrate 150, preferably in at least coarse alignment with edges that can be mechanically registered by mechanical registration feature 112. In this way a starting point for finding the location of edges of alignment structure 226 can be provided. It is assumed that alignment structure 226 has a much different resistance as measured between two points than does the underlying substrate (not shown in FIGS. 4C through 4F). For example substrate 150 can be a substantially insulating substrate and alignment structure 226 can be formed of a conductive material. Alignment structure 226 in this example is a rectangle having sides a along the X direction and b along the Y direction. Side a is made to be larger than the contact element spacing $D_x$ of probe unit 220, and side b is made to be larger than the contact element spacing $D_y$.

In FIG. 4C probe unit 220 is positioned by a controller to be near alignment structure 226 and offset along the Y direction so that it is not in contact. Probe unit 220 is then moved along the Y direction toward alignment structure 226. In FIG. 4D both first contact element 221 and second contact element 222 are in contact with alignment structure 226 (assumed here to be conductive), so that $I_1$ (FIG. 4B) indicates a high current. However, third contact element 223 is not in contact with alignment structure 226, so that $I_2$ indicates a low current. In FIG. 4E third contact element 223 has just contacted first edge 227 (FIG. 4C) of alignment structure 226, as is detected by a low to high current transition at $I_2$ that is greater than a predetermined amount. At this point, the relative motion of probe unit 220 in the Y direction is stopped, and motion in the −X direction begins. Adjacent edge 228 is identified when a high to low current transition is sensed in $I_1$ that is greater than a predetermined amount. In this way both first edge 227 and adjacent edge 228 are identified, thereby identifying the location of alignment structure 226.

FIG. 5 shows a partially exploded view of another portion of system 100 of FIG. 2. The portion of system 100 shown in FIG. 5 is configured to align a second substrate 250 having a second pattern 254 formed thereon relative to the first alignment structure(s) 152 on first substrate 150. In this example, second pattern 254 includes a two by two array of circles that are intended to be centered with respect to the two by two array of boxes of first pattern 154 on first substrate 150. Second pattern 254 can also be substantially transparent and have substantially transparent second alignment structures 252 associated with it. It is assumed in the example of FIG. 5 that the location of second alignment structures 252 have already been determined, for example, as described above relative to first alignment structures 152, and that at least one corresponding reference mark 264 has been formed on second substrate 250 at the predetermined distance and direction from the identified location of second alignment structure(s) 252. Second alignment structures 252 in FIG. 5 include rectangles that are intended to nest within the inside corners of the L-shaped first alignment structures 152.

When the second alignment structures 252 are in registration with the first alignment structures 152, then the two by two array of circles of second pattern 254 is in registration with the two by two array of boxes of first pattern 154. However, if both the first alignment structures 152 and the second alignment structures 252 are substantially transparent, it can be difficult to directly use conventional optical alignment methods. Two alternative different indirect alignment methods are shown for aligning second pattern 254 on second substrate 250 to first pattern 154 on first substrate 150 using first alignment structure 152 and second alignment structure 252. In particular, reference mark(s) 164 formed at a predetermined distance and direction from the identified location of first alignment structure(s) 152 are aligned with corresponding reference mark(s) formed at the predetermined distance and direction from the identified location of second alignment structure(s) 252. If reference marks 164 and 264 are mechanical registration marks (such as holes punched in first substrate 150 and second substrate 250 by marking element 162 (FIG. 2), then a mechanical registration member, such as pin(s) 190 can be used to register the second pattern 254 to the first pattern 154 by inserting pin(s) 190 into each set of corresponding reference marks 164 and 264. Alternatively, if reference marks 164 and 264 are optically detectable (such as registration marks made by a marking element 162 that includes an ink marker), then an optical registration member, such as camera(s) 195) can be used to register the second pattern 254 to the first pattern 154 by optical alignment of each set of corresponding visible reference marks 164 and 264.

In order to move second substrate 250 such that second pattern 254 is aligned with respect to first alignment structures 152 on first substrate 150, a registration mechanism can include a positioner 180. Second substrate 250 can be held in place on positioner 180 using vacuum, electrostatic force, or mechanical clamps for example. Controller 120 can be used to move second substrate 250 along the X and Y directions to align the second substrate 250 and then move it along the Z direction to bring the second substrate 250 into contact with the first substrate 150 for assembly, optionally with the aid of an adhesive (not shown).

In some aspects of the invention, the second alignment structure 252 is not transparent, so that its location can be optically identified prior to aligning the second substrate 250 relative to the first substrate 150. In such a case it can be advantageous to form first reference mark 164 coincident with the location of the first alignment structure 152 (that is, forming the first reference mark 164 at zero distance from the identified location of the first alignment structure. Then the second alignment structure(s) 252 can be optically aligned to first reference mark(s) 164 using camera(s) 195.

Figure 6:
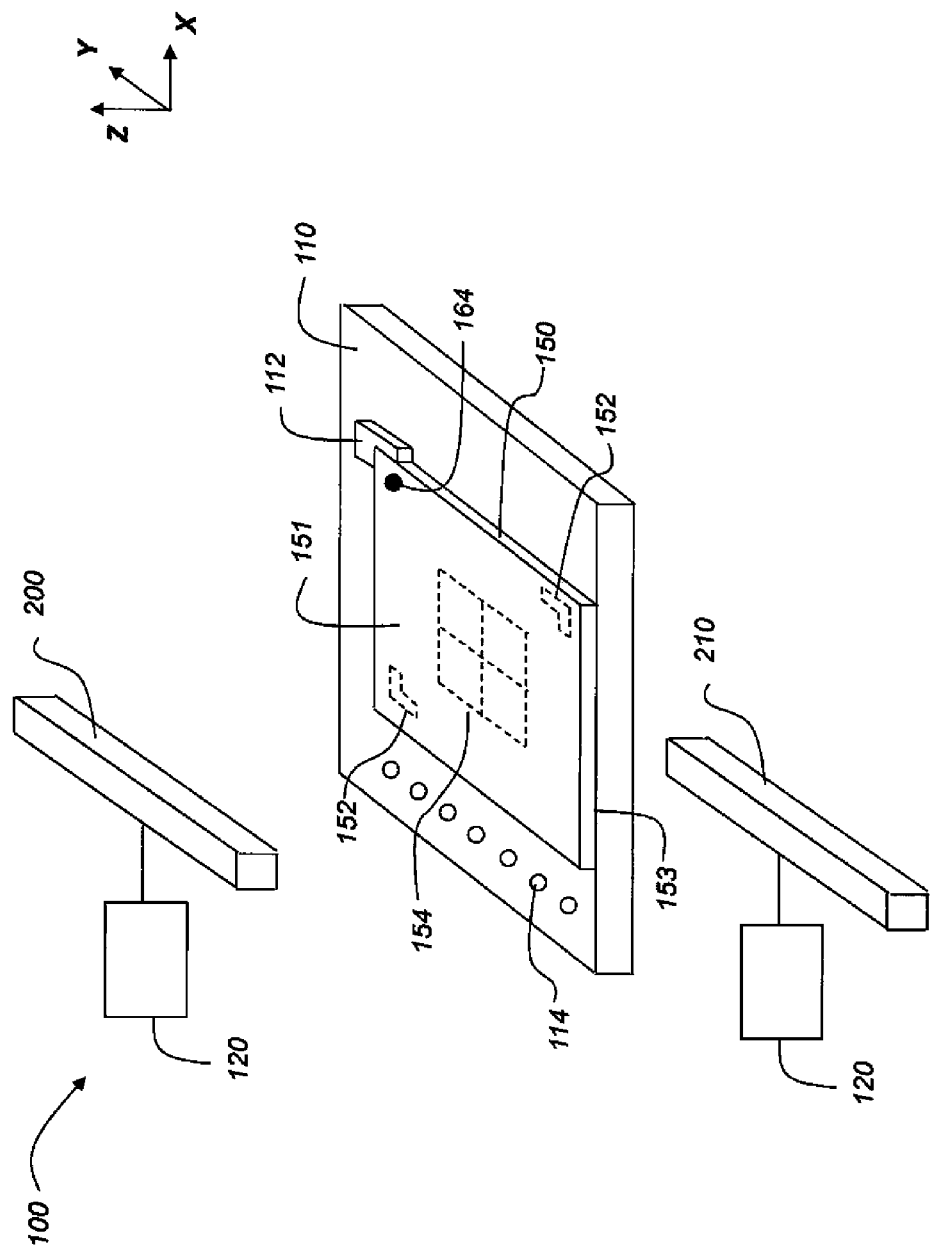
FIG. 6 shows a portion of the system of FIG. 2 for forming a second pattern in alignment with a first alignment structure.

In some aspects of the invention, alignment of a second pattern to a first pattern includes forming the second pattern on the first substrate 150 in alignment with the first alignment structure 152, rather than aligning a second substrate 250 to the first substrate 150 as described above. FIG. 6 shows a portion of system 100 (see also FIG. 2) configured for forming the second pattern in registration with the first alignment structures 152 whose locations were previously identified using electrical measurements. In FIG. 6 a pattern forming station 200 is positioned proximate the same side 151 of first substrate 150 on which first pattern 154, first alignment structures 152, and optionally reference mark(s) 164 are formed. Controller 120 can be used to control pattern forming station 200 to form a second pattern (such as second pattern 254 shown in FIG. 5) on the same side 151 of first substrate 150 as first pattern 154. Pattern forming station 200 can include an analog printing member, such as a flexographic printing plate, or a digital printhead, such as an inkjet printhead for example. Controller 120 can use locations of first alignment structures 152 previously identified and stored in memory, or it can control pattern forming station 200 relative to reference mark(s) 164 made previously relative to first alignment structures 152. The registration mechanism in these aspects of the invention includes the controller 120 and the pattern forming station 200 for forming the second pattern 254 in registration with the identified location of the first alignment structures.

Also shown in FIG. 6 is a second pattern forming station 210 positioned proximate the opposite side 153 of first substrate 150 as the side 151 on which first pattern 154, first alignment structures 152, and optionally reference mark(s) 164 are formed. Controller 120 can be used to control pattern forming station 210 to form a second pattern (such as second pattern 254 shown in FIG. 5) on the opposite side 153 of first substrate 150 as first pattern 154. Although support 110 holds first substrate 150, it is assumed here that portions of support 110 are removed that would otherwise interfere with pattern forming station 210 forming second pattern 254 on the opposite side 153.

In some aspects of the invention, alignment structures such as second alignment structures 252 shown in FIG. 5 are also formed on substrate 150. For instances where second alignment structures 252 are also substantially transparent but have values of an electrical characteristic different from that of first substrate 150, the locations of second alignment structures 252 can also subsequently be identified (for aligning additional subsequent patterns for example) using electrical measurements as described earlier.

Figure 7:
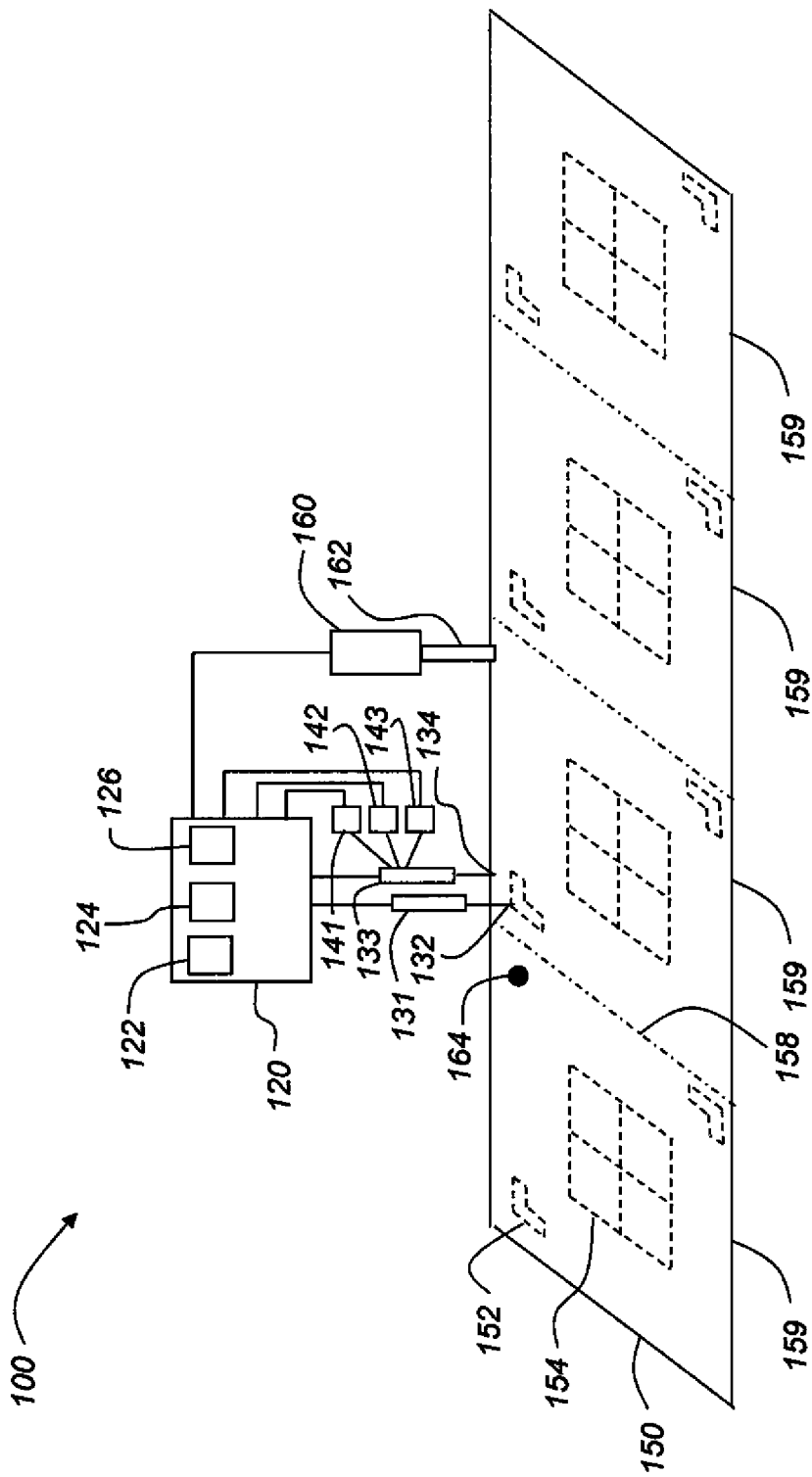
FIG. 7 shows a plurality of patterns on a substrate and a portion of the system of FIG. 2.

In some aspects of the invention, as illustrated in FIG. 7, a plurality of first substantially transparent patterns 154 are formed on first substrate 150, where each of the plurality of first substantially transparent patterns 154 includes at least one first alignment structure 152 having a magnitude of the electrical characteristic that is different from a magnitude of the electrical characteristic of the first substrate 150. First probe 131 and second probe 133 can be used to measure values of the resistance as a function of position as described above in order to identify the locations of the first alignment structures 152, and optionally marking station 160 can form reference marks 164. Subsequently, first substrate 150 can be divided along separation lines 158 into a plurality of substrate pieces 159, such that each of the plurality of substrate pieces 159 includes one of the plurality of first substantially transparent patterns 154.

Figure 8B:
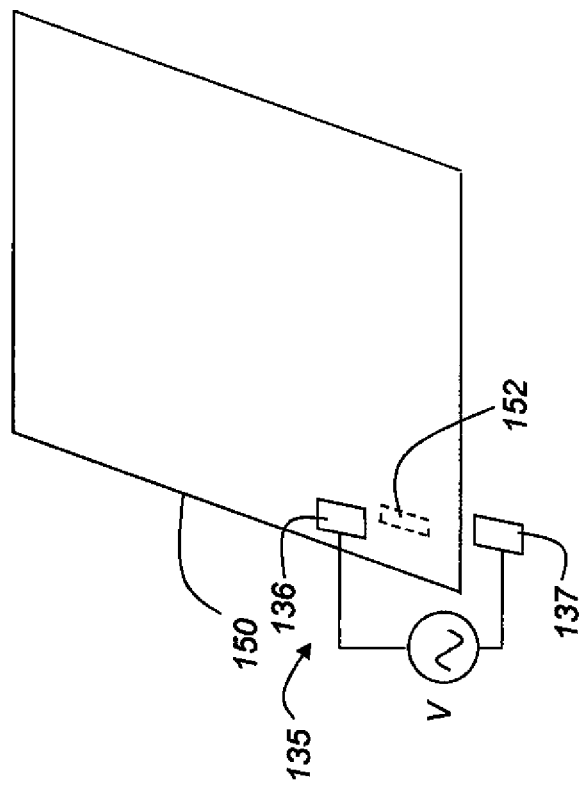
FIGS. 8A and 8B show configurations of capacitance probes.
Figure 8A:
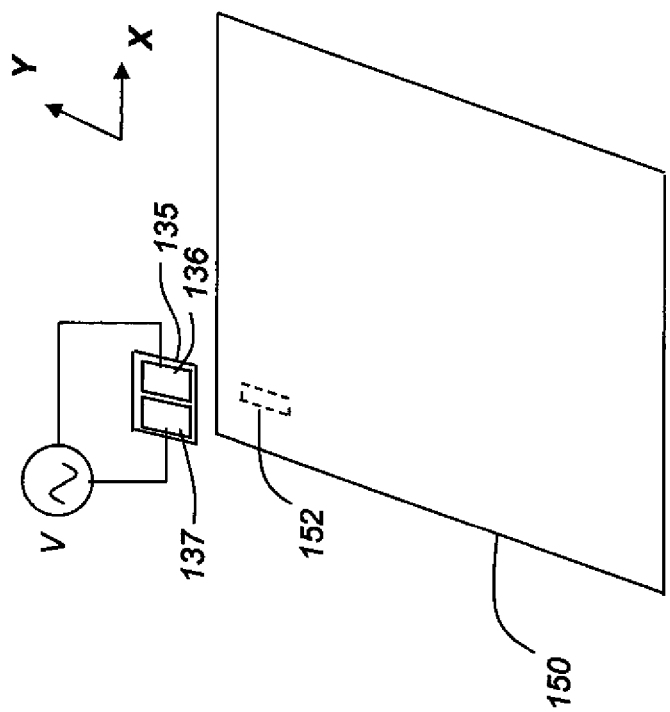

Electrical probes described above have been resistance probes that require contact with the alignment structure during measurement. Alternatively a capacitance probe 135 can be used to measure values of capacitance as a function of position (while out of contact with first substrate 150) as the capacitance probe 135 and the first substrate 150 are moved relative to each other in the X or Y directions as shown in FIGS. 8A and 8B. In the configuration shown in FIG. 8A, a pair of plates 136 and 137 are laterally displaced and electrically insulated from each other on capacitance probe 135. An AC voltage V is applied between plates 136 and 137, and a resulting electrical signal (not shown) is monitored. First alignment structure 152 can have a different resistivity or dielectric constant relative to first substrate 150. In FIG. 8B the plates 136 and 137 of capacitance probe 135 are parallel to each other and located on opposite sides of first substrate 150. As the capacitance probe is moved relative to the first substrate 150, changes in the resulting signal are used to determine the location of the alignment structure 152.

Figure 9:
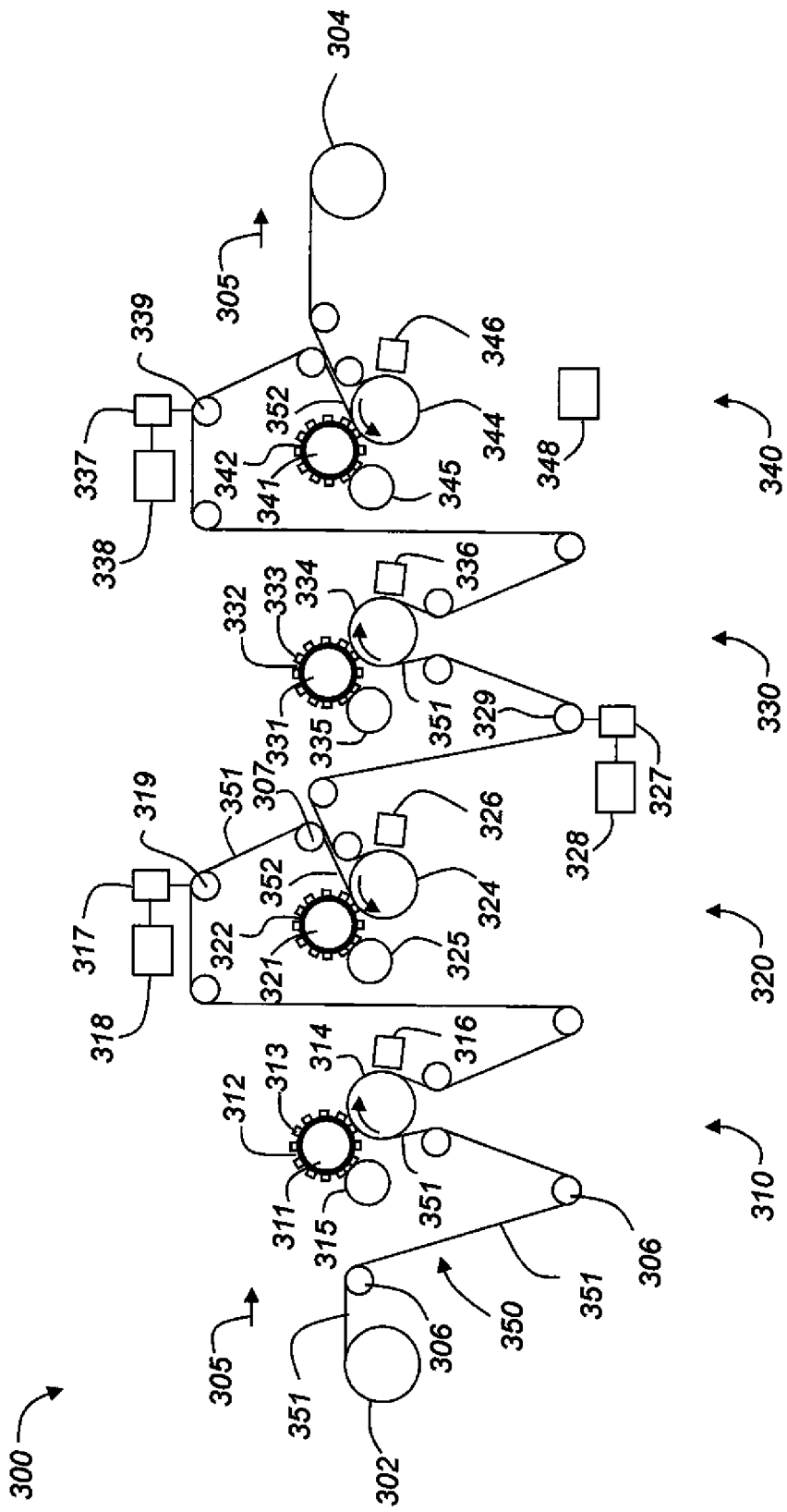
FIG. 9 is a schematic side view of a flexographic printing system that can be used in roll-to-roll aspects of the invention.

FIG. 9 is a schematic side view of a flexographic printing system 300 that can be used in aspects of the invention for roll-to-roll printing on one or both sides of a flexible substrate 350, where alignment of successive printed patterns is performed using electrical measurements to identify locations of alignment structures. Substrate 350 is fed as a web from supply roll 302 to take-up roll 304 through flexographic printing system 300. Advancement of the web can be done by a main drive roller (not shown) at or near take-up roll 304. Other drives (not shown) can be used to adjust the local speed and tension in the web. Substrate 350 has a first side 351 and a second side 352 opposite first side 351. Optionally substrate 350 is a transparent film such as PET.

The flexographic printing system 300 includes two print modules 310 and 330 that are configured to print on the first side 351 of substrate 350, as well as two print modules 320 and 340 that are configured to print on the second side 352 of substrate 350. The web of substrate 350 travels overall in roll-to-roll direction 305 (left to right in the example of FIG. 9). However, various rollers 306 and 307 are used to locally change the direction of the web of substrate as needed for adjusting web tension, providing a buffer, and reversing a side for printing. In particular, note that in print module 320 roller 307 serves to reverse the local direction of the web of substrate 350 so that it is moving substantially in a right-to-left direction.

Each of the print modules 310, 320, 330, 340 include some similar components including a respective plate cylinder 311, 321, 331, 341, on which is mounted a respective flexographic printing plate 312, 322, 332, 342, respectively. Each flexographic printing plate 312, 322, 332, 342 has raised features 313 defining an image pattern to be printed on the substrate 350. Each print module 310, 320, 330, 340 also includes a respective impression cylinder 314, 324, 334, 344 that is configured to force a side of the substrate 350 into contact with the corresponding flexographic printing plate 312, 322, 332, 342.

Each print module 310, 320, 330, 340 also includes a respective anilox roller 315, 325, 335, 345 for providing ink to the corresponding flexographic printing plate 312, 322, 332, 342. As is well known in the printing industry, an anilox roller is a hard cylinder, typically constructed of a steel or aluminum core, having an outer surface containing millions of very fine dimples, known as cells. The anilox rollers 315, 325, 335 and 345 receive the ink from ink pans or ink reservoir chambers (not shown). In some aspects of the invention, some or all of the print modules 310, 320, 330, 340 also include respective UV curing stations 316, 326, 336, 346 for curing the printed ink on substrate 350.

For conventional roll-to-roll printing of registered patterns on a substrate 350 by successive print modules 310, 320, 330 and 340, optical alignment of alignment structures would generally be used. However, when printing transparent patterns onto substrate 350, optical alignment can be difficult. According to aspects of the invention, electrical measurements using a probe (in similar fashion as described above) can be used to identify the locations of alignment structures, as long as there is sufficient "electrical contrast" between the measured electrical characteristic for the alignment structure and the substrate 350.

In a roll-to-roll printing system, such as flexographic printing system 300, the substrate 350 is moved along a path called the in-track direction from supply roll 302 to take-up roll 304. Although the path typically winds around various rollers as shown in FIG. 9, the path includes substantially straight segments in which substrate 350 moves in a predetermined substantially linear direction. Since the substrate 350 is moved in a roll-to-roll printing system, the electrical probe can be held in a fixed position, while the substrate 350 and alignment structures move past the stationary probe. FIG. 9 shows three stationary electrical probes 317, 327 and 337, as well as the corresponding controllers 318, 328 and 338. Probe 317 and controller 318 are used to identify locations of alignment structures formed on first side 351 of substrate 350 by print module 310. Probe 327 and controller 328 are used to identify locations of alignment structures formed on second side 352 of substrate 350 by print module 320. Probe 337 and controller 338 are used to identify locations of alignment structures formed on first side 351 of substrate 350 by print module 330. Identified locations of alignment structures can be stored in memory that can be included in controllers 318, 328 and 338, for example. Each of the probes 317, 327 and 337 is shown as positioned opposite a corresponding roller 319, 329, and 339 in order to stabilize the motion of the web of substrate 350 in the regions where electrical measurements are made.

The various print modules 310, 320, 330 and 340 include corresponding printing plates 312, 322, 332 and 342 that serve as pattern forming stations and are generally located between the supply roll 302 and the corresponding stationary probe 317, 327 and 337. Printing plate 322 of second print module 320 is located between stationary probe 317 and take-up roll 304. In the example of FIG. 9, there is no stationary probe downstream of the final printing plate 342, since no subsequent patterns need to be aligned to patterns printed by print module 340. However, there is a controller 348 for adjusting registration of patterns printed by fourth printing module 340. UV curing stations 316, 326 and 336 are located between corresponding printing plate 312, 322, and 332 and corresponding probes 317, 327 and 337.

As disclosed above, a gap can be provided between the surface of substrate 350 and the stationary probes 317, 327 and 337. Alternatively, the stationary probes 317, 327 and 337 can be configured to contact the surface of substrate 350. In order to keep a contact probe from removing portions of the alignment structures by scratching, the probe tip can have a rounded surface. (See FIGS. 11A and 11B.) Optionally the probe tip can have a rotatable surface, such as a rotatable ball (similar to a ballpoint pen), a rotatable cylinder or a wheel.

The stationary probes 317, 327 and 337 can be capacitance probes if the measured electrical characteristic is capacitance, or resistance probes if the measured electrical characteristic is resistance. Capacitance probes can have elements disposed on opposite sides of the substrate as shown in FIG. 8B. In some aspects of the invention, one element of the capacitance probe can be metal roller 319, 329 or 339.

After location of an alignment structure printed by first print module 310 has been determined by probe 317 and controller 318, the information is used to adjust the operation of the flexographic printing system 100 in order to form patterns by at least one successive print module 320 (on second side 352), or print module 330 (on first side 351) or print module 340 (on second side 352) in registration with the pattern and alignment structure printed by first print module 310 on first side 351 of substrate 350. In order to adjust the printing position of a subsequent pattern printed by a subsequent print module along the in-track direction (that is, to correct the longitudinal position), or along the cross-track position (that is, into or out of the plane of FIG. 9 to correct for lateral registration), or to correct for skew error, measures such as those described in U.S. Pat. No. 4,534,288 can be taken.

Figure 10:
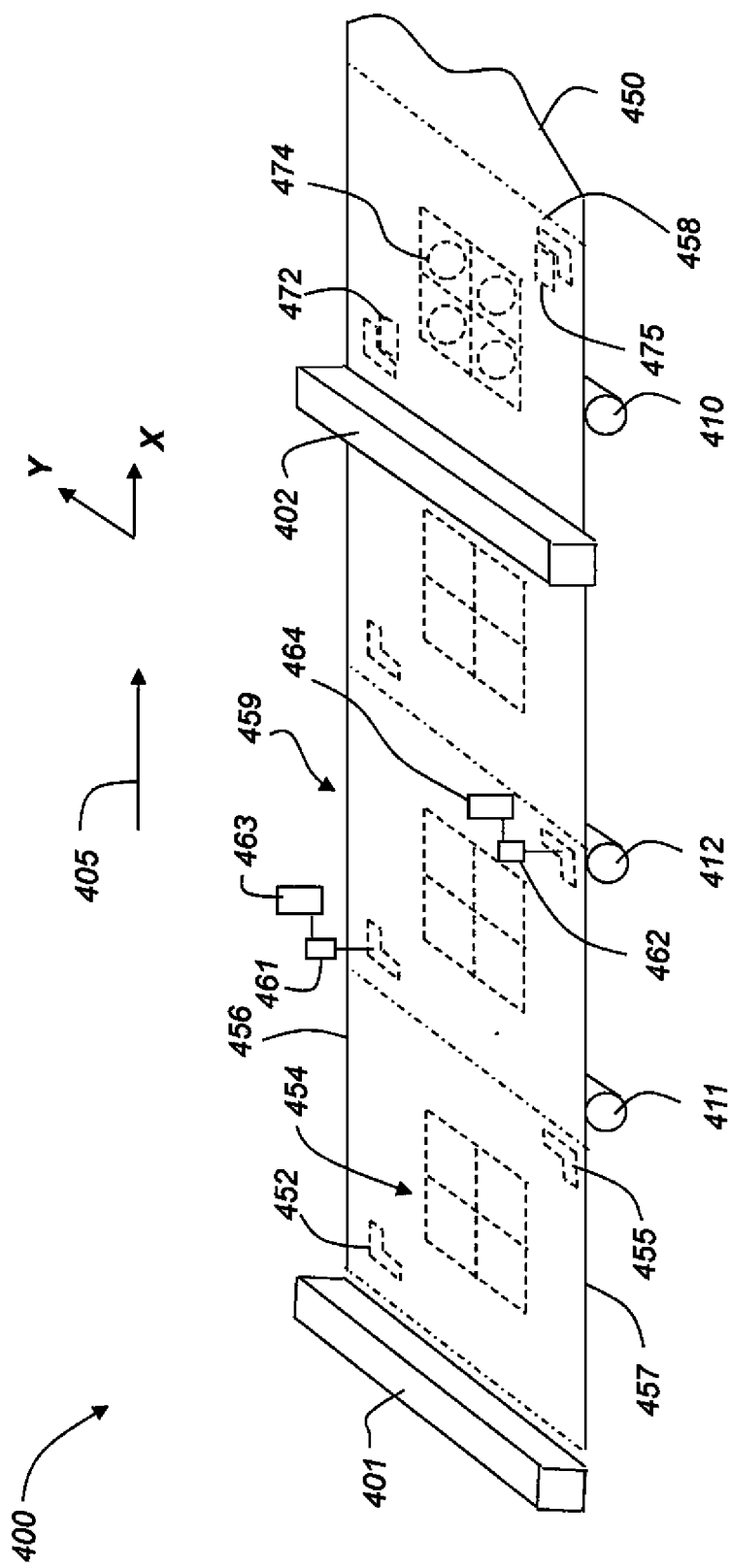
FIG. 10 shows a portion of a printing system that can be used in aspects of the invention.

A portion of printing system 400 is shown in FIG. 10. Web of substrate 450 is advanced along advancement direction 405 by drive roller 410. First pattern forming station 401 (for example a printhead) forms first pattern 454 and a plurality of first alignment structures 452 and 455 in a series of frames 459. Frames 459 are bounded at each end by separation lines 458. Separation lines 458 can be printed on substrate 450, or they can just represent the sites at which web of substrate 450 will subsequently be cut into pieces. In the example shown in FIG. 10, there are three frames between first pattern forming station 401 and second pattern forming station 402, which is configured to print second pattern 474 and a plurality of second alignment structures 472 and 475 in registration with first alignment structures 452 and 455 respectively. First alignment structure 452 and second alignment structure 472 are printed near first edge 456 of substrate 450. First alignment structure 455 and second alignment structure 475 are printed near second edge 457 of substrate 450. A first stationary probe 461 is located near first edge 456 of substrate 450 in order to make electrical measurements in line with first alignment structures 452 as substrate 450 moves past along advancement direction 405. A second stationary probe 462 is located near second edge 457 of substrate 450 in order to make electrical measurements in line with first alignment structures 455 as substrate 450 moves past along advancement direction 405. Roller 411 supports web of substrate 450 near first stationary probe 461, and roller 412 supports web of substrate 450 near second stationary probe 462. An encoder (not shown) can be attached to roller 411 or roller 412, for example, in order to monitor the movement of substrate 450. First controller 463 receives measurement signals from first stationary probe 461 and interprets them to identify positions of first alignment structures 452. Second controller 464 receives measurement signals from second stationary probe 462 and interprets them to identify positions of first alignment structures 455. First and second controllers 463 and 464 can include memories for storage of alignment structure locations. Second pattern forming structure 402 is controlled to print second pattern 474 in registration with first pattern 454 based on information provided first and second controllers 463 and 464. In the example shown in FIG. 10, first pattern 454 is a two by two array of boxes and second pattern 474 is a two by two array of circles. When second pattern 474 is registered to first pattern 454, the circles are positioned in the centers of the boxes, and the second alignment structures 472 and 475 are aligned with respect to first alignment structures 452 and 455 respectively.

Figure 11B:
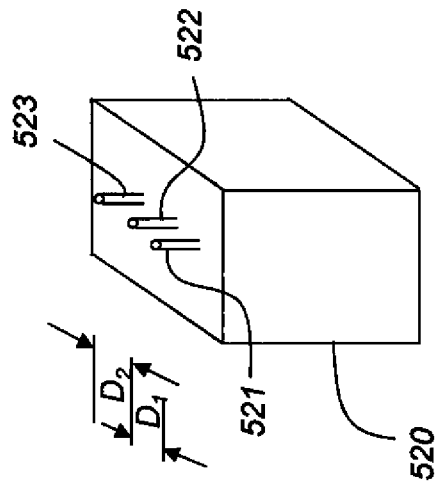
FIGS. 11A and 11B show configurations of a resistance probe unit.
Figure 11A:
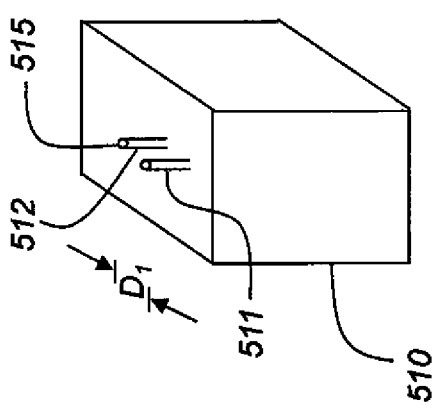

As indicated above with reference to FIG. 4A, a plurality of probe elements can be incorporated together in a single probe unit. In FIG. 11A, probe unit 510 includes two contact elements 511 and 512 that are electrically insulated from each other and spaced apart by a distance $D_1$. For aspects of the invention where the tips of contact elements 511 and 512 are held in contact with the substrate as the probe unit 510 and the substrate are moved relative to each other, it can be advantageous for contact elements 511 and 512 to have a rounded contact surface 515. Optionally, rounded contact surface can be rotatable. In FIG. 11B, probe unit 520 includes a first contact elements 521, a second contact element 522 and a third contact element 523 that are electrically insulated from each other and are arrayed in linear fashion, such that second contact element 522 is between first contact element 521 and third contact element 523. First and second contact elements 521 and 522 are spaced apart by a distance $D_1$, and second and third contact elements 522 and 523 are spaced apart by a distance $D_2$. In some aspects of the invention, as discussed below, it can be advantageous if $D_2$ is greater than $D_1$.

Figure 12:
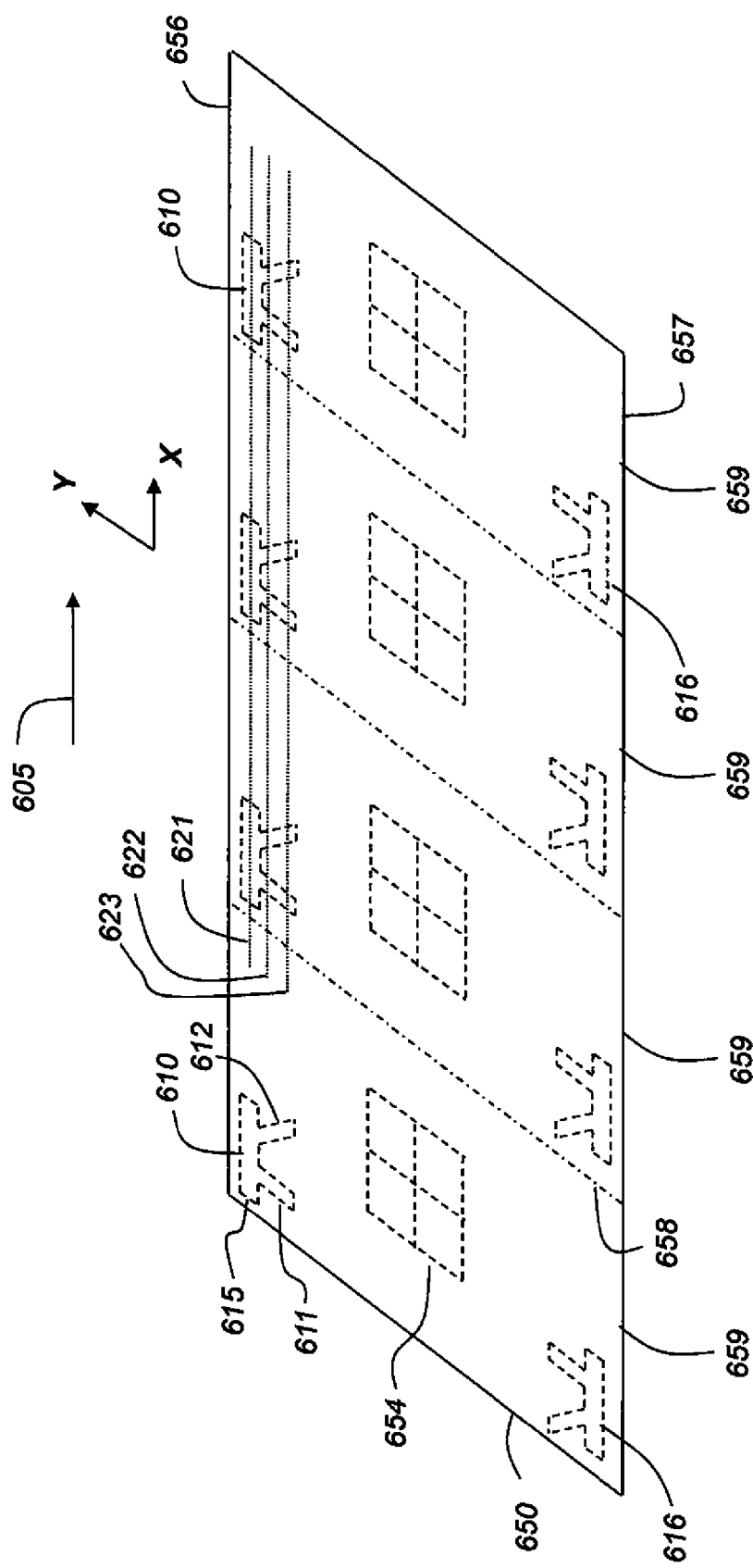
FIG. 12 shows a perspective of an alignment structure configuration according to an aspect of the invention.

In a system where the relative motion of the substrate and the probe is in a single linear direction, such as advancement direction 405 (nominally the X direction) in FIG. 10, it is useful to be able to determine alignment information along both the X direction and the Y direction using relative motion only in the X direction. FIG. 12 shows a perspective of an alignment structure configuration that can provide alignment information along both the X direction and the Y direction using a resistance measurement as the substrate is moved relative to the probe in the X direction. First and second alignment structures 610 and 616 can be formed during the same pattern forming operation that forms pattern 654, so that determining the alignment location of first or second alignment structures 610 and 616 also provides information about the location and orientation of pattern 654. First and second alignment structures 610 and 616 in FIG. 12 are not to scale, but are shown as relatively large compared to pattern 654 in order to provide better visibility for the features of the alignment structures.

Pattern 654 as well as first and second alignment structures 610 and 616 are indicated by dashed outlines to indicate that they are substantially transparent in this example. By substantially transparent it is meant that they have a light transmittance greater than 75%, and more preferably between 80% and 100%. In addition, substrate 650 has a high resistivity, for example as shown in Table 1 above, and first and second alignment structures 610 and 616 have comparatively low resistivity, for example as shown in Table 2 above. First and second alignment structures 610 and 616 can be formed using materials such as an inorganic oxide film (for example indium tin oxide) or an organic film (for example PEDOT, PDOT-PSS, graphene, or carbon nanotubes). Typically, alignment structures formed using a transparent conductive material have a resistivity between $10^{-8}$ ohm-meter and 1 ohm-meter. Properties stated below relative to first alignment structure 610 are also generally applicable to second alignment structure 616. Second alignment structure 616 can be a mirror image of first alignment structure 610 for example. The resistance measured by two probe contact elements at a predetermined distance between any two points on first alignment structure 610 is less than one percent of an electrical resistance of the substrate as measured by the same two probe contact elements at the same predetermined distance. In other words, there is a large difference in the value of resistance measured if both contact elements are in contact with first alignment structure 610, relative to the much higher resistance measured if one or both contact elements are not in contact with first alignment structure 610.

Figures 13A, 13B:
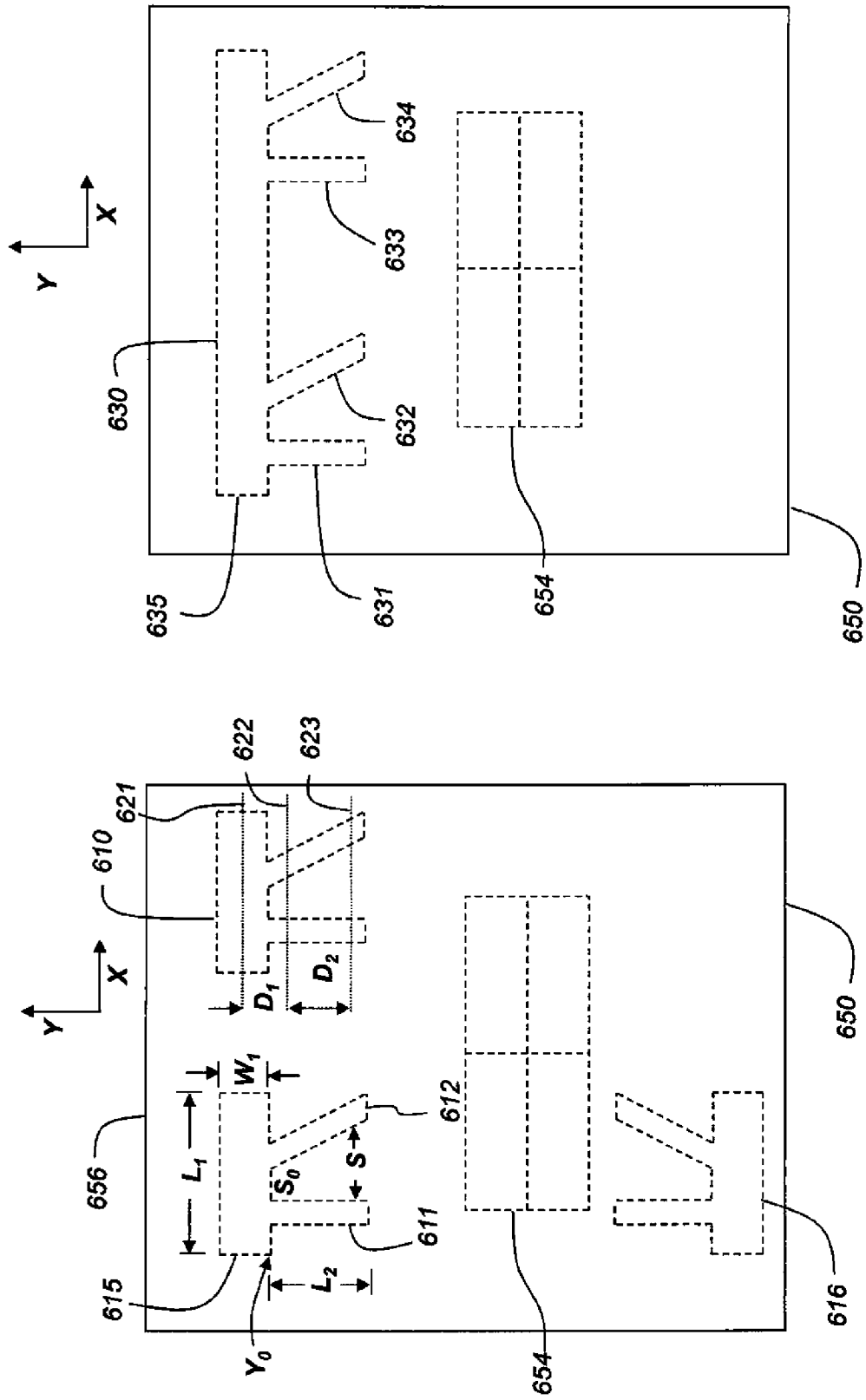
FIG. 13A shows a top view of an alignment structure similar to that shown in FIG. 12.
FIG. 13B shows a top view of an alternate alignment structure configuration.

With reference to FIG. 12 and the top view of FIG. 13A, one (or more) first alignment structure(s) 610 is formed near first edge 656 of substrate 650 and is designed to facilitate alignment by electrical resistance measurement. First alignment structure 610 includes a reference member 615 that extends along the X direction, which is nominally the advancement direction 605; a first member 611 that is connected to the reference member 615 and extends along a first direction (defined in this example to be the Y direction); and a second member 612 that is connected to the reference member 615 and is not parallel to the reference member 615 or the first member 611. In this example, first member 611 is shown as perpendicular to reference member 615, but in other aspects of the invention (not shown) first member 611 is not perpendicular to reference member 615. Dotted lines 621, 622 and 623 represent contact paths of corresponding resistance probes as substrate 650 is advanced along advancement direction 605 past stationary probes. The resistance probes can be independent from one another or can be contact elements of a probe unit 510 or 520 described above with reference to FIGS. 11A and 11B. For example, contact paths 621, 622 and 623 can represent where contact elements 521, 522 and 523 contact substrate 650 and first alignment structures 610. A high resistance value is measured between contact elements 521 and 522 unless both contact elements 521 and 522 are in contact with first alignment structure 610.

Reference member 615 of first alignment structure 610 has a length $L_1$ that is sufficiently long that the corresponding resistance probe (for example first contact element 521) will be in continuous contact with it as substrate 650 is advanced along advancement direction 605 in the region where second and third contact elements 522 and 523 can come into contact with first alignment structure 610. With reference to FIGS. 11B and 13A, suppose the substrate 650 is advanced relative to probe unit 520 such that second contact element 522 and third contact element 523 contact the leftmost edge of first member 611 first, and approximately at the same time $t_0$. Then as substrate 650 continues to be advanced, second contact element 522 and third contact element 523 contact the rightmost edge of first member 611 a bit later at $t_1$ and approximately at the same time as each other. Then as substrate 650 continues to be advanced, second contact element 522 contacts the leftmost edge of second member 612 at $t_2$. Then as substrate 650 continues to be advanced, third contact element 523 contacts the leftmost edge of second member 612 at $t_3$. At each of these edges a large change in the value of the measured resistances occurs. When a second or third contact element 522 or 523 enters the first or second member 611 or 612 of first alignment structure the corresponding value of resistance decreases dramatically. The exact resistance value is not of interest, only that it suddenly decreases. Similarly when a second or third contact element 522 or 523 exits the first or second member 611 or 612 of first alignment structure 610, the resistance value increases dramatically. Location of the leftmost edge of first member 611, either by using a clock measurement of the timing of $t_0$ and a known value of the advancement speed, or by correlating the resistance value decrease with an encoder measurement of location of substrate 650, identifies the location of first alignment structure 610 along the X direction. A further refinement of the location of first alignment structure 610 along the X direction is obtained by measuring the sudden increase of resistance at the rightmost edge of second member 612 at $t_1$. The identification of both the leftmost edge and the rightmost edge of first member 611 determines the width of first member 611 so that manufacturing variation in linewidth of first member 611 can be corrected for in determining the location of first alignment structure 610 along the X direction.

Because second member 612 is not parallel to first member 611, the location of first alignment structure 610 along the Y direction can also be identified by determining the locations where second contact element 522 exits first member 611 at $t_1$ and where second contact element 522 enters second member 612 at $t_2$, thereby indicating the spacing S between the first member 611 and the second member 612. As seen in FIG. 13A, spacing S varies along the Y direction as $S=S_0+bY$, where $S_0$ is the spacing between the first member 611 and the second member 612 where they intersect reference member 615 at $Y_0$, b is the rate of change of spacing, and Y is measured with reference to $Y_0$. Therefore the $Y_2$ position of the second contact element 522 is given by $Y_2=(S_2-S_0)/b$. The coefficient b for rate of change of spacing is known. The nominal value of $S_0$ is known, and can be corrected for manufacturing error by the linewidth measurement described above. Although it is not necessary that the first contact element 521 be targeted for the center of reference member 615 along its width $W_1$, that is a preferred target. When first alignment structure is positioned in preferred alignment relative to probe unit 520, the center of reference member 615 along width $W_1$ is in contact with first contact element 521, and second contact element 522 is spaced a known distance $D_1$ away (FIG. 11B). The preferred location $Y_2$; for second contact element 522 is given by $Y_{2i} = D_1 - W_1/2$. Measurement of the actual spacing $S_2 = S_0 + bY_2$ is used to determine the alignment error $\Delta Y$ between the actual position $Y_2$ of second contact element 522 and the preferred position $Y_{2i}$ of second contact element 522 relative to first alignment structure 610. In particular, since $Y_2 = (S_2-S_0)/b$, $$\Delta Y = Y_2 - Y_{2i} = (S_2-S_0)/b - D_1 + W_1/2.$$

An additional determination of the Y offset of first alignment structure 610 can be made in similar fashion using the resistance values measured by third contact element 523 to determine spacing $S_3$ between the rightmost edge of first member 611 and the leftmost edge of second member 612. The preferred location $Y_3$; for third contact element 523 is given by $Y_{3i} = D_1 + D2 - W_1/2$. In addition to providing a second measurement of $\Delta Y$ alignment error for improved measurement accuracy, the third contact element 523 can also provide an indication of skew, that is, rotational misalignment of first alignment structure 610 relative to advancement direction 605. Preferably, since first member 611 is perpendicular to reference member 615 in this example, and since probe unit 520 is aligned perpendicular to advancement direction 605, second contact element 522 and third contact element 523 should contact the leftmost edge of first member 611 at exactly the same time $t_0$. If the changes in resistance value are not simultaneous, there is an indication of skew.

It may not be practical, in some aspects of the invention, to have the length $L_2$ of first member 611 be sufficiently long to permit a wide enough spacing $D_2$ of second contact element 522 and third contact element 523 to provide a sufficiently accurate measurement of skew. In such aspects of the invention, a first probe unit 510 or 520 can be located near first edge 656 of substrate 650 in order to take resistance measurements of first alignment structures 610, and a second probe unit 510 or 520 can be located near the second edge 657 of substrate 650 in order to take resistance measurements of second alignment structures 616. The first and second alignment structures 610 and 616 can be formed such that if there is no rotational misalignment of pattern 654, the resistance measurements for the second members 522 will change simultaneously for first and second alignment structures 610 and 616 (assuming the two probe units near first edge 656 and second edge 657 have been properly aligned relative to each other). Determination of skew can be made by measuring differences with respect to simultaneous changes.

The desired functioning of first alignment structure 610 provides some guidelines for its design, as well as for the design of the probe contact elements. Since it is assumed that first contact element 521 will always hit reference member 615 as substrate 650 is moved along advancement direction 605 (nominally parallel to X), width $W_1$ of reference member 615 along the Y direction should be sufficiently wide that if the maximum anticipated cross-track positioning error is $\pm E$ along the Y direction, width $W_1$ should be at least 2E. Because second contact element 522 should never hit reference member 615, even if first contact element is misaligned to be at the top of reference member 615, the distance $D_1$ between first contact element 521 and second contact element 522 should be greater than W1. Because second contact element 522 should be in a position to hit first member 611 even if first contact element 521 is misaligned to be at the bottom of reference member 615, the length $L_2$ of first member 611 along a direction perpendicular to the X direction should be greater than width $W_1$ of the reference member 615 along the direction perpendicular to the X direction. In order to provide sufficient variation in spacing S between the first member 611 and the second member 612, while also having the reference member 615 extending at least as long as the furthest apart portions of first member 611 and second member 612, it can be advantageous for the length $L_1$ of reference member 615 along the X direction to be greater than the length $L_2$ of the first member 611 along the direction it extends.

As shown in FIGS. 12 and 13A, there can be a plurality of first alignment structures 610 disposed near first edge 656 of substrate 650. In some aspects of the invention, the plurality of first alignment structures 610 can be distributed as one first alignment structure 610 per piece of substrate 659 as in FIG. 12, where the pieces of substrate 659 are bounded by separation lines 658. In other aspects of the invention, there can be a plurality of first alignment structures 610 near first edge 656 in a single piece as shown in FIG. 13A. By providing a plurality of first alignment structures 610 within a piece, registration can be monitored and corrections made within a piece. The alignment structure 630 shown in FIG. 13B is related to the two first alignment structures 610 in FIG. 13A in that the reference member 635 has been lengthened along the X direction to enable resistance measurement of two pairs of members. Alignment structure 630 includes first member 631 that is connected to reference member 635 and extends along a second direction (Y in this example); second member 632 that is connected to reference member 635 and is not parallel to reference member 635 or first member 631; third member 633 that is parallel to first member 631; and fourth member 634 that is parallel to second member 632. Alignment structure 630 (or multiple copies of first alignment structure 610 near first edge 656) can provide an alternative way to measure skew where there is a probe unit only near first edge 656. In particular, the amount of skew is measured by the difference in ΔY alignment error for third member 633 and fourth member 634 minus the ΔY alignment error for first member 631 and second member 632 divided by the distance in X between the first member 631 and the third member 633.

In some aspects of the invention, reference member 615 or 635 can be preformed on substrate 650. In these aspects, first member 611 or 631, second member 612 or 632, and any other members such as third member 633 and fourth member 634 are formed at the same time as pattern 654. If pattern 654 is substantially transparent, at least first member (611 or 631) and second member (612 or 632) will also be substantially transparent. In some aspects of the invention, preformed reference member 615 or 635 is not substantially transparent, although it would still be electrically conductive.

FIG. 14A shows another example of an alignment structure configuration that can be used in a system where the relative motion of the substrate 650 and the probe is in a single linear direction, such as advancement direction 605. The alignment structure configuration includes a first alignment bar 671 located near first edge 656 of substrate 650, a second alignment bar 672 located near first alignment bar 671, and a third alignment bar 673 located near second edge 657 of substrate 650. First alignment bar 671 is tilted relative to advancement direction 605 such that it is not parallel to advancement direction 605. Second alignment bar 672 is tilted relative to advancement direction 605 such that it is not parallel to advancement direction 605 and also not parallel to first alignment bar 671. Third alignment bar 673 is parallel to second alignment bar 672. With reference to imaginary reference line 670 extending along the Y direction, it can be seen that second alignment bar 672 and third alignment bar 673 are separated along the Y direction, and have no offset relative to each other in the X direction. First alignment bar 671 is offset from second and third alignment bars 672 and 673 in both X and Y. In addition, first alignment bar 671 has an opposite slope relative to second and third alignment bars 672 and 673. In this example, the X direction is parallel to advancement direction 605, and the Y direction is parallel to the cross-track direction.

A first contact pair 661 including a first roller 662 and a second roller 663 is positioned in line with first alignment bar 671, so that as substrate 650 is advanced along advancement direction 605, first roller 662 and second roller 663 will make contact with first alignment bar 671. A second contact pair 664 including a first roller 665 and a second roller 666 is positioned in line with second alignment bar 672, so that as substrate 650 is advanced along advancement direction 605, first roller 665 and second roller 666 will make contact with second alignment bar 672 at a later time than the first contact pair 661 makes contact with the first alignment bar 671, due to the offset along Y of the second alignment bar 672. A third contact pair 667 including a first roller 668 and a second roller 669 is positioned in line with third alignment bar 673, so that as substrate 650 is advanced along advancement direction 605, first roller 668 and second roller 669 will make contact with third alignment bar 673 at about the same time than the second contact pair 664 makes contact with the second alignment bar 672. In one aspect of the invention, all of the rollers in the contact pairs 661, 664 and 667 are conductive and are optionally mounted in pairs on insulating shafts 660.

A simplified diagram of first contact pair 661 and associated circuitry is shown in FIG. 14B. Connected between first roller 662 and second roller 663 is a voltage V and a current measuring device I. As substrate 650 is advanced along advancement direction 605, first and second rollers 662 and 663 make contact with substrate 650 and first alignment bar 671 as indicated by the dashed lines. Because of the slope of first alignment bar 671, second roller 663 will first make contact with first alignment bar 671 at second entry edge 676. As substrate 650 continues to advance along advancement direction 605, first roller 662 next makes contact with first alignment bar 671 at first entry edge 675. Up to this point the current has been low but now makes a transition from low to high (as shown by current $I_1$ in FIG. 14C), thereby identifying the position of first entry edge 675. Current stays high until second roller 663 leaves first alignment bar 671 at second exit edge 678, resulting in a high to low transition (as shown by current $I_1$ in FIG. 14C), thereby identifying the position of second exit edge 678. The spacing of first and second rollers 662 and 663 and the geometry of first alignment bar 671 are then used to determine the location of first alignment bar 671. Similarly, second contact pair 664 and third contact pair 667 are monitored for current transitions as shown respectively by currents $I_2$ and $I_3$ in FIG. 14C. Based on the speed of the substrate 650 along advancement direction 605 and the known amount X offset of the second and third alignment bars 672 and 673, there will be a time interval $t_a$ between the current pulse in $I_1$ and the current pulse in $I_2$. Similarly there will be a time interval $t_b$ between the current pulse in $I_1$ and the current pulse in $I_2$. If $t_a$ and $t_b$ are both equal to the same predetermined time interval, then there is no alignment error of substrate 650 along the Y cross track direction. Alignment errors along the cross track direction can be determined because the slopes of the second and third alignment bars 672 and 673 are different from the slope of the first alignment bar 671. With reference to FIG. 14A, if substrate 650 is moved to the right in the Y direction, first contact pair 661 will make contact with first alignment bar 671 a bit later than nominal, and second contact pair 664 will make contact with second alignment bar 672 a bit earlier than nominal. As a result, as shown in FIG. 14D, the time interval $t_a$ will be shorter than the predetermined time interval shown in FIG. 14C. If the substrate had been moved to the left, the time interval would be longer than the predetermined time interval (not shown). In FIG. 14D $t_a=t_b$, so even though the substrate 650 is misaligned in Y, there is no skew error. Skew error is identified when $t_a$ does not equal $t_b$ as in FIG. 14E.

In the examples described above, measurement of resistance has been done between two contact elements. It is known that two point resistance measurements are susceptible to error due to contact resistance, such as that due to poor surface contact. FIG. 15A shows an example of resistance measurements of alignment structures where two outer contact elements (first current contact 681 and second current contact 682) are used to provide current from a current source $I_S$, and two voltage measurements are made at first voltage contact 683 and second voltage contact 684 relative to a central reference contact 685. Optionally the five contact elements 681-685 can be contained in a single probe unit similar to those of FIG. 11B or 14B. A continuous chevron alignment structure 680 having two legs 686 and 687, which are neither parallel to each other nor to advancement direction 605, makes contact with contacts 681-685 as the substrate (not shown) moves in advancement direction 605. Voltage transitions between first voltage contact 683 and reference contact 685 and between second voltage contact 684 and reference contact 685 indicate edges of continuous chevron alignment structure 680 in similar fashion as described above.

Figure 15B:
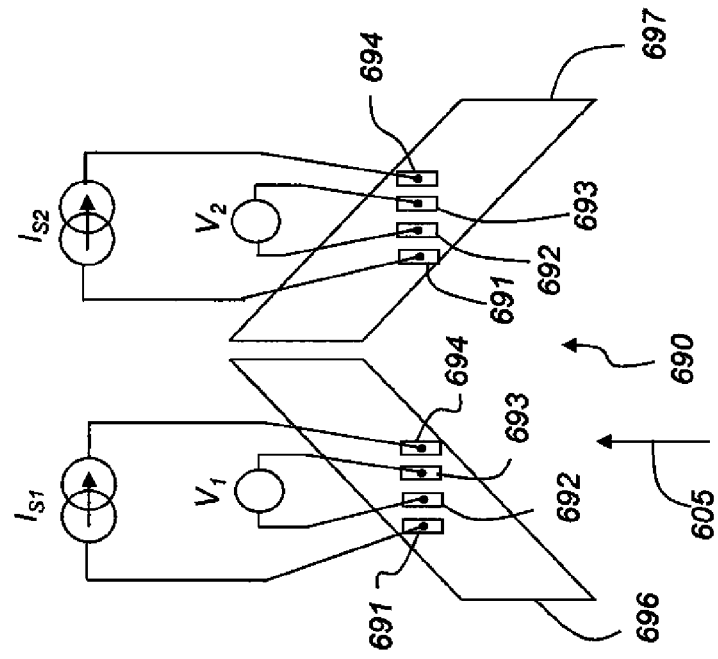
FIGS. 15A and 15B show further alignment structure configurations according to aspects of the invention.
Figure 15A:
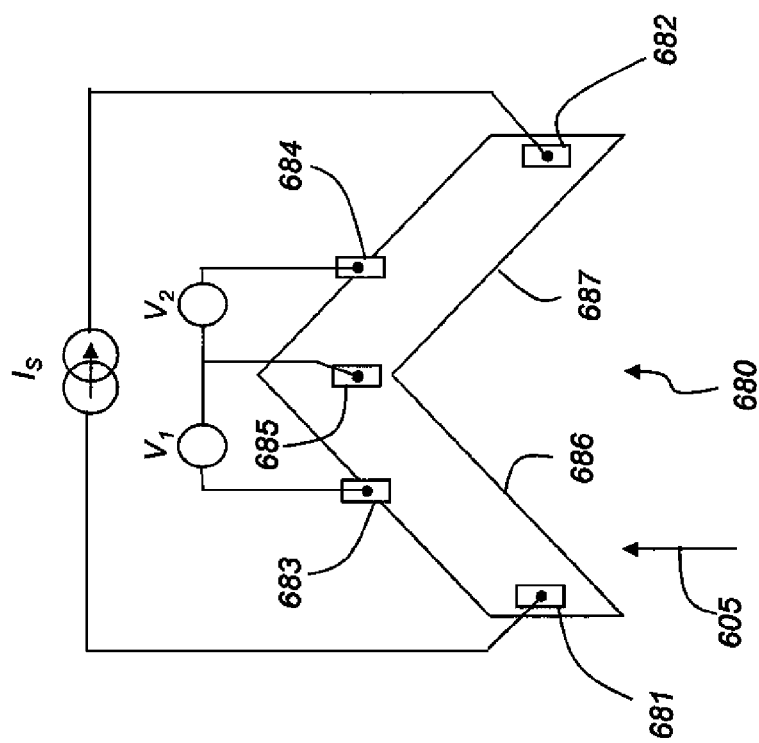

FIG. 15B shows an example of resistance measurements on a split chevron alignment structure 690 having two legs 696 and 697, which are neither parallel to each other nor to advancement direction 605. Four point resistance measurements are made independently on each leg 696 and 697. For leg 696 current is provided by current source $I_{S1}$ at outer contacts 691 and 694 and voltage $V_1$ is read across inner contacts 692 and 693. Similarly current source $I_{S2}$ is used to provide current to outer contacts 691 and 694 and voltage V2 is measured across inner contacts 692 and 693 for leg 697.

Figure 16:
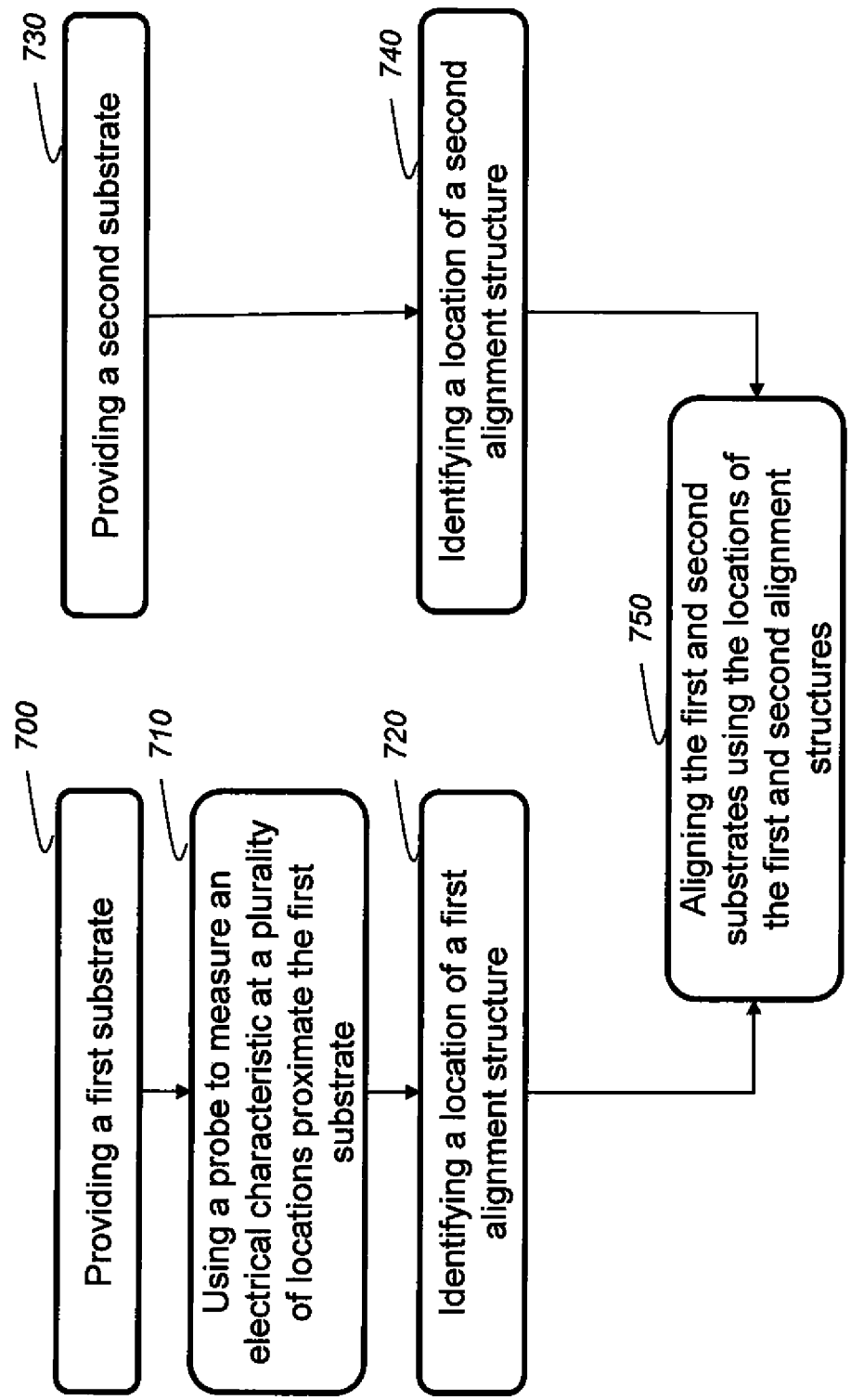
FIG. 16 shows a flowchart for a method for aligning patterns on two substrates according to an aspect of the invention.

FIG. 16 shows a flowchart for a method for aligning a second pattern to a first pattern based on a first alignment structure having a location identified by measurements of an electrical characteristic according to an aspect of the invention. In Step 700, a first substrate having a first pattern including the first alignment structure is provided. The first alignment structure has a different magnitude of the electrical characteristic than the first substrate. In Step 710, an electrical probe is used to measure the electrical characteristic corresponding to each of a plurality of positions proximate the first substrate. In Step 730 the measured electrical characteristic are compared as a function of position of the probe to identify a location of the first alignment structure. The location of the first alignment structure can be identified by a difference between the measured electrical characteristic at a pair of the plurality of positions exceeding a predetermined threshold. The threshold can be set to any value appropriate for detecting the location of the alignment structure. As an example, the threshold can be set to be a difference of at least an order of magnitude at a pair of a plurality of locations. In Step 730, a second substrate having the second pattern including a second alignment structure is provided. In Step 740, the location of the second alignment structure is identified. In Step 750, the second substrate is aligned to the first substrate using the identified locations of the first and second alignment structures.

In an aspect of the invention, Step 750 can further include the following steps. A first reference feature is provided at a first distance and direction from the identified location of the first alignment structure. A second reference feature is provided at second distance and direction from the identified location of the second alignment feature. The first and second reference features are used to align the second substrate to the first substrate. The first reference feature can include a first hole in the first substrate, and the second reference feature can include a second hole in the second substrate. In this example, the first and second reference features are used to align the second substrate to the first substrate by inserting a pin through both the first hole in the first substrate and the second hole in the second substrate. The predetermined distance can be set to any value, including zero.

In some aspects of the invention, the first alignment structure is substantially transparent but the second alignment structure is non-transparent. In these aspects, the location of the non-transparent second alignment structure can be optically identified. In another aspect of the invention, the method for aligning the patterns can further include a plurality of first substantially transparent patterns on the first substrate, each of the plurality of first substantially transparent patterns including at least one first alignment structure having associated therewith a magnitude of the electrical characteristic that is different from a magnitude of the electrical characteristic of the first substrate. The probe is used to measure the electrical characteristic at a plurality of locations to identify locations of each of the first alignment structures associated with each of the plurality of first substantially transparent patterns. The first substrate is divided into a plurality of substrate pieces using the identified locations of each of the first alignment structures such that each of the plurality of substrate pieces includes one of the plurality of first substantially transparent patterns.

In various aspects of the invention, the electrical characteristic can be resistance or capacitance. In an aspect of the invention, identifying the location of the first alignment structure includes identifying at least one position along a first edge of the first alignment structure and at least one position along a second edge of the first alignment structure. The first edge can be disposed on a first side of a first member of the alignment structure and the second edge can be disposed on a second side of the first member of the alignment structure. In other aspects of the invention, the first edge can be disposed on a first member of the alignment structure, and the second edge can be disposed on a second member of the alignment structure.

In some aspects of the invention, the electrical probe can be moved to measure the electrical characteristic corresponding to each of the plurality of positions proximate the first substrate. In these aspects of the invention, the electrical probe includes a probe unit having a first contact element, a second contact element, and a third contact element that are electrically insulated from each other and arrayed in nonlinear fashion. The probe unit is moved in a first direction until the electrical characteristic measured between the first contact element and the second contact element differs by a first amount exceeding the predetermined threshold to identify a first edge of the first alignment structure. The probe unit can then be moved in a second direction, not parallel to the first direction, until the electrical characteristic measured between the first contact element and the third contact element differs by a second amount exceeding the predetermined threshold to identify a second edge of the first alignment structure. The second direction can be perpendicular to the first direction.

In other aspects of the invention, the first substrate can be moved relative to the electrical probe to measure the electrical characteristic corresponding to each of the plurality of positions proximate the first substrate.

A system for aligning a second pattern to a first pattern based on a first alignment structure having a location identified by measurements of an electrical, according to an aspect of the invention, can comprise of:

(i) a first substrate having the first pattern including the first alignment structure, wherein the first alignment structure has a different magnitude of the electrical characteristic than the first substrate.

(ii) an electrical probe.

(iii) a controller for controlling the relative position of the electrical probe with respect to the first substrate to measure the electrical characteristic corresponding to each of a plurality of positions proximate the first substrate, for comparing the measured electrical characteristic as a function of position of the probe to identify the location of the first alignment structure by identifying a difference between the measured electrical characteristic at a pair of the plurality of positions exceeding a predetermined threshold.

(iv) a second substrate having the second pattern including a second alignment structure formed thereon.

(v) a controller for identifying the location of the second alignment structure. This controller can be the same controller as in element (iii) or a different controller.

(vi) a registration mechanism for aligning the second substrate to the first substrate using the identified locations of the first and second alignment structures.

The system can also include a support for the first substrate, the support including a hold-down mechanism for the first substrate. The system can also include movers for moving the probe. A first mover can be provided for moving the probe along a first direction that is parallel to the support for the first substrate or the first substrate. In this aspect of the invention, a controller can be configured to control the probe to take a first measurement at a first position, move the probe to a second position that is a first distance along the first direction, and take a second measurement at the second position. In another aspect of the invention, the controller can be further configured to control the probe to move the probe to a third position that is a second distance along the first direction and take a third measurement at the third position, wherein the second distance is less than the first distance if the second measurement corresponds to a proximity of the first alignment structure. Alternately, the controller can be further configured to control the probe to move the probe to a third position that is a second distance along a direction opposite the first direction and take a third measurement at the third position, wherein second distance is less than the first distance. The system can also include a second mover for moving the probe along a second direction that is parallel to the support for the first substrate or the first substrate and not parallel to the first direction. A third mover can move the probe along a third direction that is perpendicular to the support for the first substrate or the first substrate to move the probe into and out of contact with the first substrate.

In various aspects of the invention, the probe can be a resistance probe or a capacitance probe. The system is not limited to a single probe but can have alternate arrangements including multiple probes. In some aspects of the invention, the movers move the support for the first substrate or the first substrate, rather than the probe. For example, the first mover can move the support for the first substrate or the first substrate along a first direction that is parallel to the support for the substrate. The second mover can move the support for the first substrate or the first substrate along a second direction that is parallel to the support for the first substrate or the first substrate and not parallel to the first direction.

In some aspects of the invention, the registration mechanism can include a marking station for providing at least one reference mark on the first substrate at a distance and direction, determined by the controller, from the identified location of the first alignment structure. The marking station includes at least one of an ink marker, a laser, a blade a drill, a heated tip, an indenter or a hole punch to make the reference mark. The registration mechanism can further include a positioner for positioning a second substrate on which the second pattern is formed relative to the first substrate such that the pattern is aligned relative to the first alignment structure on the first substrate.

Figure 17:
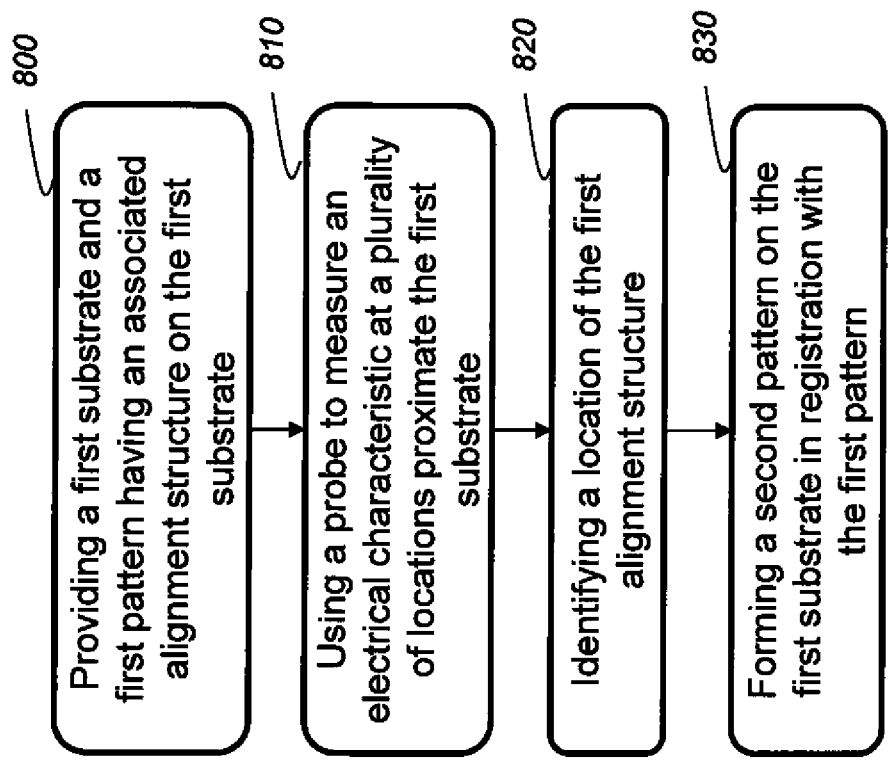
FIG. 17 shows a flowchart for a method for aligning two patterns on a substrate according to an aspect of the invention.

FIG. 17 shows a flowchart for a method for forming a second pattern in registration with a first pattern on a substrate, according to an aspect of the invention. In Step 800, a first substrate, having an associated first magnitude of an electrical characteristic, and a first pattern on a surface of the first substrate, the first pattern including at least one alignment structure that is associated with a second magnitude of the electrical characteristic that is different from the first magnitude of the electrical characteristic of the substrate, is provided. In Step 810, an electrical probe is used to measure the electrical characteristic corresponding to each of a plurality of positions proximate the substrate, wherein the measured electrical characteristic corresponds to the alignment structure when the probe is proximate to the alignment structure, and the measured electrical characteristic corresponds to the substrate when the probe is not proximate to the alignment structure. In Step 820, a controller is used to interpret the measured electrical characteristics for identifying a location of the alignment structure. In Step 830, the identified location of the alignment structure is used to control the forming of the second pattern such that it is in registration with the first pattern. The substrate can be moved proximate the probe along a predetermined direction.

In an aspect of the invention, moving the substrate further includes using an advancement mechanism to feed the substrate from a supply roll, past the stationary probe, and toward a take-up roll. The first pattern is formed on the surface of the substrate at a pattern forming station located between the supply roll and the stationary probe. A curing station can be located between the pattern forming station and the stationary probe. In another aspect of the invention, there can be a gap between the surface of the substrate and the probe.

The probe for measuring capacitance can include elements disposed on opposite sides of the substrate. The probe for measuring resistance can be configured to contact the surface of the substrate. The probe can include a rounded contact surface or a rotatable contact surface. The probe can also include a plurality of contact members that are electrically insulated from each other.

In various aspects of the invention, the second pattern is formed on a same surface of the substrate as the first pattern. In other aspects of the invention, the first pattern is formed on a first surface of the substrate, and the second pattern is formed on a second surface that is on the opposite side of the substrate from the first surface. The first pattern, the alignment structure, the second pattern, or the substrate can be substantially transparent.

In an aspect of the invention, a system for forming a second pattern in registration with an alignment structure of a first pattern on a substrate comprises:

(i) an advancing mechanism for moving the substrate.

(ii) a stationary probe for measuring an electrical characteristic at a plurality of positions proximate the moving substrate.

(iii) a controller for interpreting the measured electrical characteristic as a function of position for identifying a location of the alignment structure.

(iv) a patterning station for forming the second pattern on a surface of the substrate in registration with the first pattern based on the identified location of the alignment structure.

The advancing mechanism can include movers for moving the substrate past the stationary probe along a first direction and a second direction different from the first direction.

In another aspect of the invention, a system for determining an alignment location associated with a pattern formed on a substrate by making electrical measurements as the substrate is moved along an advancement direction comprises:

(i) an alignment structure formed on the substrate, the alignment structure having a first member extending along a first direction that is not parallel to the advancement direction and a second member extending along a second direction that is not parallel to either the advancement direction or to the first member, wherein the first member and the second member are electrically conductive and substantially transparent.

(ii) one or more probes responsive to relative motion between the substrate and the probe to identify particular portions of the first and second members of the alignment structure and produce signals identifying such portions.

(iii) a controller responsive to signals produced by the probe to determine an alignment location associated with the pattern formed on the substrate.

In some aspects of the invention, the alignment structure can further include a reference member extending along a direction parallel to the advancement direction and intersecting both the first and second members. Each of the first member and second members of the alignment structure has a light transmittance, preferably, between 80% and 100%. Further, each of the first and second members of the alignment structure has a resistivity, preferably, between $10^{-8}$ ohm-meter and 1 ohm-meter. In some aspects of the invention, each of the first and second members of the alignment structure has an electrical resistance that is less than one percent of an electrical resistance of the substrate as measured by two contacts that are positioned a predetermined distance apart.

In various aspects of the invention, the members of the alignment structure can include an inorganic oxide film or an organic film. The inorganic oxide film can be include poly(3, 4-ethylenedioxythiophene), grapheme, orcarbon nanotubes.

The invention has been described in detail with particular reference to certain preferred aspects of the invention, but it will be understood that variations and modifications can be effected within the spirit and scope of the invention. And even though specific aspects of the invention have been described herein, it should be noted that the application is not limited to these aspects of the invention. In particular, any features described with respect to one aspect may also be used in other aspects of the invention, where compatible. And the features of the different aspects of the invention may be exchanged, where compatible.

PARTS LIST 10 mask aligner
15 camera
20 exposure station
25 radiation
30 first mask
32 first pattern
34 boxes
35 alignment mark
36 alignment mark
40 second mask
42 second pattern
44 circles
45 alignment mark
46 alignment mark
50 substrate
52 pattern
54 boxes
55 alignment mark
56 alignment mark
58 photoresist
62 pattern
64 boxes
65 alignment mark
66 alignment mark
100 system
110 support
112 mechanical registration feature
114 vacuum holes
120 controller
122 measurement module
124 registration module
126 mover control module
131 first probe
132 probe tip
133 second probe
134 probe tip
135 capacitance probe
136 plate
137 plate
141 first mover
142 second mover
143 third mover
150 first substrate
151 side of first substrate
152 first alignment structure
153 opposite side of first substrate
154 first pattern
156 edge
158 separation line
159 substrate piece
160 marking station
162 marking element
164 reference mark
170 contact position
171 first position
172 second position
173 third position
176 first position
177 second position
178 third position
180 positioner
190 pin
191 first mover
192 second mover
195 camera
200 pattern forming station
210 pattern forming station
220 probe unit
221 first contact element
222 second contact element
223 third contact element
225 contact surface
226 alignment structure
227 first edge
228 adjacent edge
250 second substrate
252 second alignment structure
254 second pattern
264 reference mark
300 flexographic printing system
302 supply roll
304 take-up roll
305 roll-to-roll direction
306 roller
307 roller
310 print module
311 plate cylinder
312 printing plate
313 raised features
314 impression cylinder
315 anilox roller
316 curing station
317 probe
318 controller
319 roller
320 print module
321 plate cylinder
322 printing plate
324 impression cylinder 325 anilox roller
326 curing station
327 probe
328 controller
329 roller
330 print module
331 plate cylinder
332 printing plate
334 impression cylinder
335 anilox roller
336 curing station
337 probe
338 controller
339 roller
340 print module
341 plate cylinder
342 printing plate
344 impression cylinder
345 anilox roller
346 curing station
348 controller
350 substrate
351 first side
352 second side
400 printing system
401 first pattern forming station
402 second pattern forming station
405 advancement direction
410 drive roller
411 roller
412 roller
450 substrate
452 first alignment structure
454 first pattern
455 another first alignment structure
456 first edge
457 second edge
458 separation line
459 frame
461 first stationary probe
462 second stationary probe
463 first controller
464 second controller
472 second alignment structure
474 second pattern
475 another second alignment structure
510 probe unit
511 contact element
512 contact element
515 contact surface
520 probe unit
521 first contact element
522 second contact element
523 third contact element
605 advancement direction
610 first alignment structure
611 first member
612 second member
615 reference member
616 second alignment structure
621 contact path
622 contact path
623 contact path
630 alignment structure
631 first member
632 second member
633 third member
634 fourth member
635 reference member
650 substrate
654 pattern
656 first edge
657 second edge
658 separation line
659 substrate piece
660 shaft
661 first contact pair
662 first roller
663 second roller
664 second contact pair
665 first roller
666 second roller
667 third contact pair
668 first roller
669 second roller
670 reference line
671 first alignment bar
672 second alignment bar
673 third alignment bar
675 first entry edge
676 second entry edge
677 first exit edge
678 second exit edge
680 contiguous chevron alignment structure
681 first current contact
682 second current contact
683 first voltage contact
684 second voltage contact
685 reference contact
686 leg
687 leg
690 split chevron alignment structure
691 outer contact
692 inner contact
693 inner contact
694 outer contact
696 leg
697 leg
700 Step of providing a first substrate
710 Step of using a probe to measure an electrical characteristic at a plurality of locations proximate the first substrate
720 Step of identifying a location of a first alignment structure
730 Step of providing a second substrate
740 Step of identifying a location of a second alignment structure
750 Step of aligning the first and second substrates using the locations of the first and second alignment structures
800 Step of providing a first substrate and a first pattern having an associated alignment structure on the first substrate
810 Step of using a probe to measure an electrical characteristic at a plurality of locations proximate the first substrate
820 Step of identifying a location of the first alignment structure
830 Step of forming a second pattern on the first substrate in registration with the first pattern

The invention claimed is:

1. A system for aligning a second pattern to a first pattern based on a first alignment structure having a location identified by measurements of an electrical characteristic, comprising:
a first substrate having the first pattern including the first alignment structure, wherein the first alignment structure has a different magnitude of the electrical characteristic than the first substrate;

an electrical probe;

a controller for controlling the relative position of the electrical probe with respect to the first substrate to measure the electrical characteristic corresponding to each of a plurality of positions at or near the first alignment structure, for comparing the measured electrical characteristic as a function of position of the electrical probe to identify the location of the first alignment structure by identifying a difference between the measured electrical characteristic at a pair of the plurality of positions exceeding a predetermined threshold;

a second substrate having the second pattern including a second alignment structure formed thereon;

a controller for identifying the location of the second alignment structure; and a registration mechanism for aligning the second substrate to the first substrate using the identified locations of the first and second alignment structures.

2. The system of claim 1, further including a support for the first substrate that includes a hold-down mechanism for the first substrate.

3. The system of claim 1, further including a first mover for moving the electrical probe along a first direction that is parallel to the first substrate.

4. The system of claim 3, wherein the controller is configured to control the electrical probe to take a first measurement at a first position, move the electrical probe to a second position that is a first distance along the first direction, and take a second measurement at the second position.

5. The system of claim 4, wherein the controller is configured to control the electrical probe to move the electrical probe to a third position that is a second distance along the first direction and take a third measurement at the third position, wherein the second distance is less than the first distance if the second measurement corresponds to a proximity of the first alignment structure.

6. The system of claim 4, wherein the controller is configured to control the electrical probe to move the electrical probe to a third position that is a second distance along a direction opposite the first direction and take a third measurement at the third position, wherein second distance is less than the first distance.

7. The system of claim 3, further including a second mover for moving the electrical probe along a second direction that is parallel to the first substrate and not parallel to the first direction.

8. The system of claim 3, further including a third mover for moving the electrical probe along a third direction that is perpendicular to the first substrate to move the electrical probe into and out of contact with the first substrate.

9. The system of claim 1, wherein the electrical probe is a resistance probe.

10. The system of claim 1, wherein the electrical probe is a capacitance probe.

11. The system of claim 1, further including a second electrical probe for measuring the electrical characteristic.

12. The system of claim 1, further including a first mover for moving the first substrate along a first direction that is parallel to the first substrate.

13. The system of claim 12, further including a second mover for moving the first substrate along a second direction that is parallel to the first substrate and not parallel to the first direction.

14. The system of claim 1, wherein the registration mechanism further includes a marking station for providing at least one reference mark on the substrate at a distance and direction determined by the controller, from the identified location of the first alignment structure.

15. The system of claim 14, wherein the marking station includes at least one of an ink marker, a laser, a blade a drill, a heated tip, an indenter or a hole punch.

16. The system of claim 1, wherein the registration mechanism further includes a positioner for positioning the second substrate relative to the first substrate so that the second pattern is aligned with the first pattern relative to the first and second alignment structures on the first and second substrates respectively.

* * * * *